United States Patent
Kralicky et al.

(10) Patent No.: US 11,179,209 B2
(45) Date of Patent: *Nov. 23, 2021

(54) AUTONOMOUS CORRECTION OF ALIGNMENT ERROR IN A MASTER-SLAVE ROBOTIC SYSTEM

(71) Applicant: Titan Medical Inc., Toronto (CA)

(72) Inventors: Joseph Kralicky, North Kingstown, RI (US); Peter Cameron, Menlo Park, CA (US)

(73) Assignee: Titan Medical Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/060,470

(22) Filed: Oct. 1, 2020

(65) Prior Publication Data

US 2021/0015569 A1    Jan. 21, 2021

Related U.S. Application Data

(63) Continuation of application No. 16/411,537, filed on May 14, 2019, now Pat. No. 10,820,953, which is a
(Continued)

(51) Int. Cl.
*A61B 34/37*    (2016.01)
*A61B 34/35*    (2016.01)
(Continued)

(52) U.S. Cl.
CPC ............ *A61B 34/37* (2016.02); *A61B 17/29* (2013.01); *A61B 34/35* (2016.02); *A61B 34/74* (2016.02);
(Continued)

(58) Field of Classification Search
CPC ......... A61B 34/37; A61B 34/35; A61B 34/74; A61B 17/29; A61B 2034/301;
(Continued)

(56) References Cited

U.S. PATENT DOCUMENTS 7,535,411 B2    5/2009  Falco
7,806,891 B2    10/2010 Nowlin et al.
(Continued)

FOREIGN PATENT DOCUMENTS

CA       2 827 589        2/2012
WO    WO 2007/014470 A2   2/2007

OTHER PUBLICATIONS

Google Search Results, Jul. 8, 2021, 1 pp. (Year: 2021).*
(Continued)

*Primary Examiner* — Toan M Le
(74) *Attorney, Agent, or Firm* — Knobbe Martens Olson & Bear LLP

(57) ABSTRACT

In some embodiments, correcting an alignment error between an end effector of a tool associated with a slave and a master actuator associated with a master in a robotic system involves receiving at the master, master actuator orientation signals ($R_{MCURR}$) representing the orientation of the master actuator relative to a master reference frame and generating end effector orientation signals ($R_{EENEW}$) representing the end effector orientation relative to a slave reference frame, producing control signals based on the end effector orientation signals, receiving an enablement signal for selectively enabling the control signals to be transmitted from the master to the slave, responsive to a transition of the enablement signal from not active state to active state, computing the master-slave misalignment signals ($R_A$) as a difference between the master actuator orientation signals ($R_{MCURR}$) and the end effector orientation signals ($R_{EENEW}$), and adjusting the master-slave misalignment signals ($R_A$) to reduce the alignment difference.

20 Claims, 12 Drawing Sheets

Related U.S. Application Data continuation of application No. 15/542,356, filed as application No. PCT/CA2016/000006 on Jan. 8, 2016, now Pat. No. 10,327,856.

(60) Provisional application No. 62/101,731, filed on Jan. 9, 2015.

(51) Int. Cl.

| | |
|---|---|
| *B25J 3/04* | (2006.01) |
| *B25J 9/16* | (2006.01) |
| *A61B 34/00* | (2016.01) |
| *A61B 17/29* | (2006.01) |
| *B25J 11/00* | (2006.01) |
| *A61B 34/30* | (2016.01) |

(52) U.S. Cl.
CPC .............. *B25J 3/04* (2013.01); *B25J 9/1689* (2013.01); *B25J 11/008* (2013.01); *A61B 2034/301* (2016.02); *A61B 2034/306* (2016.02); *G05B 2219/39024* (2013.01); *G05B 2219/40195* (2013.01); *Y10S 901/06* (2013.01); *Y10S 901/31* (2013.01)

(58) Field of Classification Search
CPC ..... A61B 2034/306; B25J 9/1689; B25J 3/04; B25J 11/008; G05B 2219/40195; G05B 2219/39024; Y10S 901/06; Y10S 901/31
See application file for complete search history.

(56) References Cited

U.S. PATENT DOCUMENTS

| | | | |
|---|---|---|---|
| 8,423,186 B2 | 4/2013 | Itkowsitz et al. | |
| 10,159,536 B2 | 12/2018 | Kralicky et al. | |
| 10,327,856 B2* | 6/2019 | Kralicky | A61B 34/35 |
| 10,820,953 B2* | 11/2020 | Kralicky | A61B 34/74 |
| 2002/0055795 A1 | 5/2002 | Niemeyer | |
| 2014/0148808 A1 | 5/2014 | Inkpen et al. | |
| 2018/0271607 A1 | 9/2018 | Kralicky et al. | |
| 2019/0201147 A1 | 7/2019 | Kralicky et al. | |
| 2019/0269472 A1 | 9/2019 | Kralicky et al. | |

OTHER PUBLICATIONS

International Search Report for International Application No. PCT/CA2016/000006 dated Mar. 30, 2016 in 4 pages.
Written Opinion for International Application No. PCT/CA2016/000006 dated Mar. 30, 2016 in 5 pages.

* cited by examiner

Modify misalignment matrix using the correction matrix
$R_\Delta' = R_\Delta R_C$ — 250

Re-compute end effector orientation $R_{EENEW}$ using
$R_{EENEW} = R_{MCURR} R_\Delta$ — 252

FIG. 8E

Compute the offset angle between the master and the slave z-axes
$\phi_{EE\_TO\_MASTER} = \operatorname{acos}(R_{EENEW}(1,3) * R_{MCURR}(1,3) + R_{EENEW}(2,3) * R_{MCURR}(2,3) + R_{EENEW}(3,3) * R_{MCURR}(3,3))$ — 205

FIG. 9

AUTONOMOUS CORRECTION OF ALIGNMENT ERROR IN A MASTER-SLAVE ROBOTIC SYSTEM

CROSS-REFERENCE TO RELATED APPLICATIONS

This application is a continuation of U.S. patent application Ser. No. 16/411,537, filed on May 14, 2019, and issued as U.S. Pat. No. 10,820,953, which is a continuation of U.S. patent application Ser. No. 15/542,356, filed on Jul. 7, 2017, and issued as U.S. Pat. No. 10,327,856, which is a U.S. national stage of International Application No. PCT/CA2016/000006, filed on Jan. 8, 2016, which claims priority to U.S. Provisional Application No. 62/101,731, filed on Jan. 9, 2015. Each of these applications is incorporated by reference in its entirety.

BACKGROUND OF THE INVENTION

1. Field of Invention

This invention relates to master-slave robotic systems such as used for laparoscopic surgery and more particularly to autonomous correction of alignment error between the master and slave in such systems.

2. Description of Related Art

During operation of a teleoperated robotic minimally invasive surgical system where a slave instrument is intended to follow the motion of a master input controller held by a user, it is possible for the master and slave to become misaligned with respect to each other's base frames of reference. In instances of misalignment, the slave end-effector no longer points in the direction that the user is expecting, which may result in less than optimal controllability of the slave instrument.

U.S. Pat. No. 7,806,891 entitled "Repositioning and reorientation of master slave relationship in minimally invasive telesurgery" describes a system but the system disrupts motion of the slave when there is misalignment between the master and slave. The system also requires a master controller with the ability to actively control, or lock orientation degrees of freedom.

U.S. Pat. No. 8,423,186 entitled "Ratcheting for master alignment of a teleoperated minimally invasive surgical instrument" describes a system that only reduces alignment error when the motion of the master handle is in a direction such that it would reduce the misalignment if the slave were not moved.

SUMMARY OF THE INVENTION

The disclosure describes a method of correcting an alignment error between an end effector of a tool associated with a slave and a master actuator associated with a master in a master-slave robotic system in which an orientation of the end effector is remotely controlled by an orientation of the master actuator by producing and transmitting control signals at the master for controlling the slave. The method involves causing a processor associated with the master to receive master actuator orientation signals ($R_{MCURR}$) representing the orientation of the master actuator relative to a master reference frame and causing the processor to generate end effector orientation signals ($R_{EENEW}$) representing the end effector orientation relative to a slave reference frame, in response to the master actuator orientation signals ($R_m$), master base orientation signals ($R_{MBASE}$) representing previous-saved values of the master actuator orientation signals ($R_{MCURR}$) and slave base orientation signals ($R_{EEBASE}$) representing previous-saved values of the end effector orientation signals ($R_{EENEW}$). The method also involves causing the processor to produce control signals based on the end effector orientation signals, for transmission from the master to the slave and causing the processor to receive an enablement signal for selectively enabling the control signals to be transmitted from the master to the slave whereby the master transmits the control signals to the slave when the enablement signal is active and does not transmit the control signals to the slave when the enablement signal is not active and such that when the enablement signal is active, changes in the orientation of the master actuator cause corresponding changes in the orientation of the end effector and such that when the enablement signal is not active, changes in the orientation of the master actuator do not cause corresponding changes in the orientation of the end effector. The method also involves, when the enablement signal transitions from the not active state to the active state, causing the processor to save the values of the master actuator orientation signals ($R_{MCURR}$) as the master base orientation signals ($R_{MBASE}$) to create the previous-saved values of the master actuator orientation signals ($R_{MCURR}$) and save the values of the end effector orientation signals ($R_{EENEW}$) as the slave base orientation signals ($R_{EEBASE}$) to create the previous-saved values of the end effector orientation signals ($R_{EENEW}$). The method also involves causing the processor to detect a difference, between the master actuator orientation signals ($R_{MCURR}$) and the end effector orientation signals ($R_{EENEW}$), the difference representing a difference in physical alignment between the tool and the master relative to their respective reference frames and in response to detecting the difference, causing the processor to adjust the saved slave base orientation signals ($R_{EEBASE}$) to ultimately have the same values as the saved master base orientation ($R_{MBASE}$) values so that subsequent generations of the end effector orientation signals ($R_{EENEW}$) cause the control signals to cause the tool to satisfy an alignment criterion.

The disclosure also describes a method of correcting an alignment error between an end effector of a tool associated with a slave and a master actuator associated with a master in a master-slave robotic system in which an orientation of the end effector is remotely controlled by an orientation of the master actuator by producing and transmitting control signals at the master for controlling the slave. The method involves causing a processor associated with the master to receive master actuator orientation signals ($R_{MCURR}$) representing the orientation of the master actuator relative to a master reference frame and causing the processor to generate end effector orientation signals ($R_{EENEW}$) representing the end effector orientation relative to a slave reference frame, in response to the master actuator orientation signals ($R_{MCURR}$) and master-slave misalignment signals ($R_A$), representing a product of previously saved values of the master actuator orientation signals ($R_{MCURR}$) and the end effector orientation signals ($R_{EENEW}$). The method also involves causing the processor to produce control signals based on the end effector orientation signals, for transmission from the master to the slave and causing the processor to receive an enablement signal for selectively enabling the control signals to be transmitted from the master to the slave whereby the master transmits the control signals to the slave when the enablement signal is active and does not transmit the control signals to the slave when the enablement signal is not active and such that when the enablement signal is active, changes in the orientation of the master actuator cause corresponding changes in the orientation of the end effector and such that when the enablement signal is not active, changes in the orientation of the master actuator do not cause corresponding changes in the orientation of the end effector. The method also involves, when the enablement signal transitions from the not active state to the active state, causing the processor to compute the master-slave misalignment signals ($R_A$) as a difference between the master actuator orientation signals ($R_{MCURR}$) and the end effector orientation signals ($R_{EENEW}$), the misalignment signals representing a difference in physical alignment between the tool and the master relative to their respective reference frames. The method further involves causing the processor to detect a second difference between the master actuator orientation signals ($R_{MCURR}$) and the end effector orientation signals ($R_{EENEW}$) the second difference representing a difference in physical alignment between the tool and the master relative to their respective reference frames and in response to detecting the second difference, causing the processor to adjust the master-slave misalignment signals ($R_A$) to reduce the alignment difference to satisfy an alignment criterion so that subsequent generations of the end effector orientation signals ($R_{EENEW}$) cause the control signals to cause the tool to be physically aligned with the master within the alignment criterion.

The disclosure also describes an apparatus for correcting an alignment error between an end effector of a tool associated with a slave and a master actuator associated with a master in a master-slave robotic system in which an orientation of the end effector is remotely controlled by an orientation of the master actuator by producing and transmitting control signals at the master for controlling the slave. The apparatus includes means associated with the master for receiving master actuator orientation signals ($R_{MCURR}$) representing the orientation of the master actuator relative to a master reference frame and means for generating end effector orientation signals ($R_{EENEW}$) representing the end effector orientation relative to a slave reference frame, in response to the master actuator orientation signals ($R_m$), master base orientation signals ($R_{MBASE}$) representing previous-saved values of the master actuator orientation signals ($R_{MCURR}$) and slave base orientation signals ($R_{EEBASE}$) representing previous-saved values of the end effector orientation signals ($R_{EENEW}$). The apparatus also includes means for producing control signals based on the end effector orientation signals, for transmission from the master to the slave and means for receiving an enablement signal for selectively enabling the control signals to be transmitted from the master to the slave whereby the master transmits the control signals to the slave when the enablement signal is active and does not transmit the control signals to the slave when the enablement signal is not active and such that when the enablement signal is active, changes in the orientation of the master actuator cause corresponding changes in the orientation of the end effector and such that when the enablement signal is not active, changes in the orientation of the master actuator do not cause corresponding changes in the orientation of the end effector. The apparatus also includes means responsive to a transition of the enablement signal from the not active state to the active state, for saving the values of the master actuator orientation signals ($R_{MCURR}$) as the master base orientation signals ($R_{MBASE}$) to create the previous-saved values of the master actuator orientation signals ($R_{MCURR}$) and saving the values of the end effector orientation signals ($R_{EENEW}$) as the slave base orientation signals ($R_{EEBASE}$) to create the previous-saved values of the end effector orientation signals ($R_{EENEW}$). The apparatus also includes means for detecting a difference, between the master actuator orientation signals ($R_{MCURR}$) and the end effector orientation signals ($R_{EENEW}$), the difference representing a difference in physical alignment between the tool and the master relative to their respective reference frames means for causing the processor to adjust the saved slave base orientation signals ($R_{EEBASE}$) to ultimately have the same values as the saved master base orientation ($R_{MBASE}$) values so that subsequent generations of the end effector orientation signals ($R_{EENEW}$) cause the control signals to cause the tool to satisfy an alignment criterion, in response to detecting the difference.

The disclosure also describes an apparatus for correcting an alignment error between an end effector of a tool associated with a slave and a master actuator associated with a master in a master-slave robotic system in which an orientation of the end effector is remotely controlled by an orientation of the master actuator by producing and transmitting control signals at the master for controlling the slave. The apparatus includes means associated with the master for receiving master actuator orientation signals ($R_{MCURR}$) representing the orientation of the master actuator relative to a master reference frame and means for generating end effector orientation signals ($R_{EENEW}$) representing the end effector orientation relative to a slave reference frame, in response to the master actuator orientation signals ($R_{MCURR}$) and master-slave misalignment signals ($R_A$), representing a product of previously saved values of the master actuator orientation signals ($R_{MCURR}$) and the end effector orientation signals ($R_{EENEW}$). The apparatus also includes means for producing control signals based on the end effector orientation signals, for transmission from the master to the slave and means for receiving an enablement signal for selectively enabling the control signals to be transmitted from the master to the slave whereby the master transmits the control signals to the slave when the enablement signal is active and does not transmit the control signals to the slave when the enablement signal is not active and such that when the enablement signal is active, changes in the orientation of the master actuator cause corresponding changes in the orientation of the end effector and such that when the enablement signal is not active, changes in the orientation of the master actuator do not cause corresponding changes in the orientation of the end effector. The apparatus also includes means responsive to a transition of the enablement signal from the not active state to the active state, for computing the master-slave misalignment signals ($R_A$) as a difference between the master actuator orientation signals ($R_{MCURR}$) and the end effector orientation signals ($R_{EENEW}$), the misalignment signals representing a difference in physical alignment between the tool and the master relative to their respective reference frames, means for detecting a second difference, between the master actuator orientation signals ($R_{MCURR}$) and the end effector orientation signals ($R_{EENEW}$) the second difference representing the difference in physical alignment between the tool and the master relative to their respective reference frames and means responsive to detecting the second difference, for causing the processor to adjust the master-slave misalignment signals ($R_A$) to reduce the alignment difference to satisfy an alignment criterion so that subsequent generations of the end effector orientation signals ($R_{EENEW}$) cause the control signals to cause the tool to be physically aligned with the master within the alignment criterion.

The disclosure also describes an apparatus for correcting an alignment error between an end effector of a tool associated with a slave and a master actuator associated with a master in a master-slave robotic system in which an orientation of the end effector is remotely controlled by an orientation of the master actuator by producing and transmitting control signals at the master for controlling the slave. The apparatus includes a processor associated with the master operably configured to receive master actuator orientation signals ($R_{MCURR}$) representing the orientation of the master actuator relative to a master reference frame. The processor is further configured to generate end effector orientation signals ($R_{EENEW}$) representing the end effector orientation relative to a slave reference frame, in response to the master actuator orientation signals ($R_m$), to generate master base orientation signals ($R_{MBASE}$) representing previous-saved values of the master actuator orientation signals ($R_{MCURR}$) and to generate slave base orientation signals ($R_{EEBASE}$) representing previous-saved values of the end effector orientation signals ($R_{EENEW}$). The process is also configured to produce control signals based on the end effector orientation signals, for transmission from the master to the slave and to receive an enablement signal for selectively enabling the control signals to be transmitted from the master to the slave whereby the master transmits the control signals to the slave when the enablement signal is active and does not transmit the control signals to the slave when the enablement signal is not active and such that when the enablement signal is active, changes in the orientation of the master actuator cause corresponding changes in the orientation of the end effector and such that when the enablement signal is not active, changes in the orientation of the master actuator do not cause corresponding changes in the orientation of the end effector. The processor is also configured to, when the enablement signal transitions from the not active state to the active state, save the values of the master actuator orientation signals ($R_{MCURR}$) as the master base orientation signals ($R_{MBASE}$) to create the previous-saved values of the master actuator orientation signals ($R_{MCURR}$) and save the values of the end effector orientation signals ($R_{EENEW}$) as the slave base orientation signals ($R_{EEBASE}$) to create the previous-saved values of the end effector orientation signals ($R_{EENEW}$). The processor is also configured to detect a difference, between the master actuator orientation signals ($R_{MCURR}$) and the end effector orientation signals ($R_{EENEW}$), the difference representing a difference in physical alignment between the tool and the master relative to their respective reference frames and the processor is configured to adjust the saved slave base orientation signals ($R_{EEBASE}$) to ultimately have the same values as the saved master base orientation ($R_{MBASE}$) values so that subsequent generations of the end effector orientation signals ($R_{EENEW}$) cause the control signals to cause the tool to satisfy an alignment criterion, in response to detecting the difference.

The disclosure also describes an apparatus for correcting an alignment error between an end effector of a tool associated with a slave and a master actuator associated with a master in a master-slave robotic system in which an orientation of the end effector is remotely controlled by an orientation of the master actuator by producing and transmitting control signals at the master for controlling the slave. The apparatus includes a processor associated with the master and operably configured to receive master actuator orientation signals ($R_{MCURR}$) representing the orientation of the master actuator relative to a master reference frame. The processor is further configured to generate end effector orientation signals ($R_{EENEW}$) representing the end effector orientation relative to a slave reference frame, in response to the master actuator orientation signals ($R_{MCURR}$) and master-slave misalignment signals ($R_A$), representing a product of previously saved values of the master actuator orientation signals ($R_{MCURR}$) and the end effector orientation signals ($R_{EENEW}$). The processor is also configured to produce control signals based on the end effector orientation signals, for transmission from the master to the slave and receive an enablement signal for selectively enabling the control signals to be transmitted from the master to the slave whereby the master transmits the control signals to the slave when the enablement signal is active and does not transmit the control signals to the slave when the enablement signal is not active and such that when the enablement signal is active, changes in the orientation of the master actuator cause corresponding changes in the orientation of the end effector and such that when the enablement signal is not active, changes in the orientation of the master actuator do not cause corresponding changes in the orientation of the end effector. The processor is also configured to, in response to a transition of the enablement signal from the not active state to the active state, compute the master-slave misalignment signals ($R_A$) as a difference between the master actuator orientation signals ($R_{MCURR}$) and the end effector orientation signals ($R_{EENEW}$), the misalignment signals representing a difference in physical alignment between the tool and the master relative to their respective reference frames. The processor is also configured to detect a second difference, between the master actuator orientation signals ($R_{MCURR}$) and the end effector orientation signals ($R_{EENEW}$) the second difference representing the difference in physical alignment between the tool and the master relative to their respective reference frames and responsive to detecting the second difference, the processor adjusts the master-slave misalignment signals ($R_A$) to reduce the alignment difference to satisfy an alignment criterion so that subsequent generations of the end effector orientation signals ($R_{EENEW}$) cause the control signals to cause the tool to be physically aligned with the master within the alignment criterion.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention,

FIGS. 8A-8E are successive portions of a flowchart representing codes executed by the master apparatus of the laparoscopic surgery system shown in FIG. 1, to provide for computation of an alignment difference between the input device shown in FIG. 2 and the end effector shown in FIG. 4 and for controlling translational movement of the end effector and for controlling the type of control signals sent to a slave subsystem of the laparoscopic surgery system shown in FIG. 1, based on the computed alignment difference; and FIG. 9 is a flowchart of an alternative block of code optionally replacing the block of code shown at 204 and 206 in FIG. 8B.

DETAILED DESCRIPTION

Figure 1:
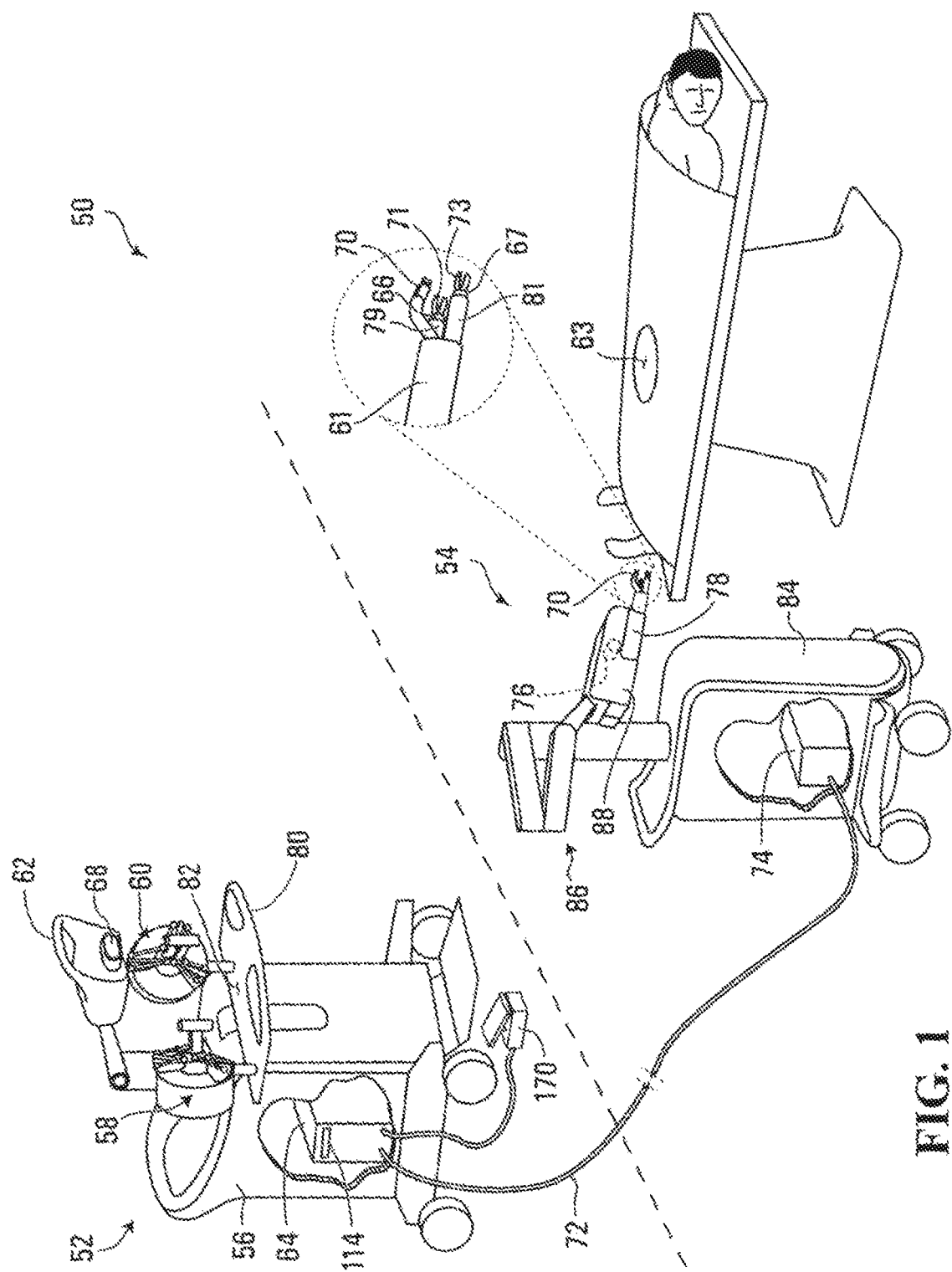
FIG. 1 is a pictorial representation of a laparoscopic surgery system according to one embodiment of the invention.

Referring to FIG. 1, a robotic control system in the form of a laparoscopic surgery system is shown generally at 50. The system includes a master subsystem 52 and a slave subsystem 54. The master subsystem 52 may be located anywhere in the world, but for the purposes of this description it will be considered to be in an operating room. The slave subsystem 54 is located in the operating room.

In the embodiment shown, the master subsystem 52 comprises a workstation 56 having first and second input devices 58 and 60 and a viewer 62 in communication with a master apparatus 64 comprising at least one processor. The first and second input devices 58 and 60 are operable to be actuated by respective hands of an operator such as a surgeon, for example, who will perform the laparoscopic surgery by manipulating the first and second input devices of the master subsystem 52 to control corresponding laparoscopic tools 66 and 67 on the slave subsystem 54.

The viewer 62 may include an LCD display 68, for example, for displaying images acquired by a camera 70 on the slave subsystem 54, to enable the user to see the laparoscopic tools 66 and 67 inside the patient while manipulating the first and second input devices 58 and 60 to cause the tools to move in desired ways to perform the surgery. The first and second input devices 58 and 60 produce position and orientation signals that are received by the master apparatus 64 and the master apparatus produces slave control signals that are transmitted by wires 72 or wirelessly, for example, from the master subsystem 52 to the slave subsystem 54.

The slave subsystem 54 includes a slave computer 74 that receives the slave control signals from the master subsystem 52 and produces motor control signals that control motors 76 on a drive mechanism of a tool controller 78 of the slave subsystem 54, to extend and retract wires (not shown) of respective tool positioning devices 79 and 81 to position and to rotate the tools 66 and 67. Exemplary tool positioning devices and tools for this purpose are described in PCT/CA2013/001076, which is incorporated herein by reference. The tool positing devices 79 and 81 extend through an insertion tube 61, a portion of which is inserted through a small opening 63 in the patient to position end effectors 71 and 73 of the tools 66 and 67 inside the patient, to facilitate the surgery.

In the embodiment shown, the workstation 56 has a support 80 having a flat surface 82 for supporting the first and second input devices 58 and 60 in positions that are comfortable to the operator whose hands are actuating the first and second input devices 58 and 60.

In the embodiment shown, the slave subsystem 54 includes a cart 84 in which the slave computer 74 is located. The cart 84 has an articulated arm 86 mechanically connected thereto, with a tool holder mount 88 disposed at a distal end of the articulated arm.

In the embodiment shown, the first and second input devices 58 and 60 are the same, but individually adapted for left and right hand use respectively. In this embodiment, each input device 58 and 60 is an Omega.7 haptic device available from Force Dimension, of Switzerland. For simplicity, only input device 60 will be described, it is being understood that input device 58 operates in the same way.

Figure 2:
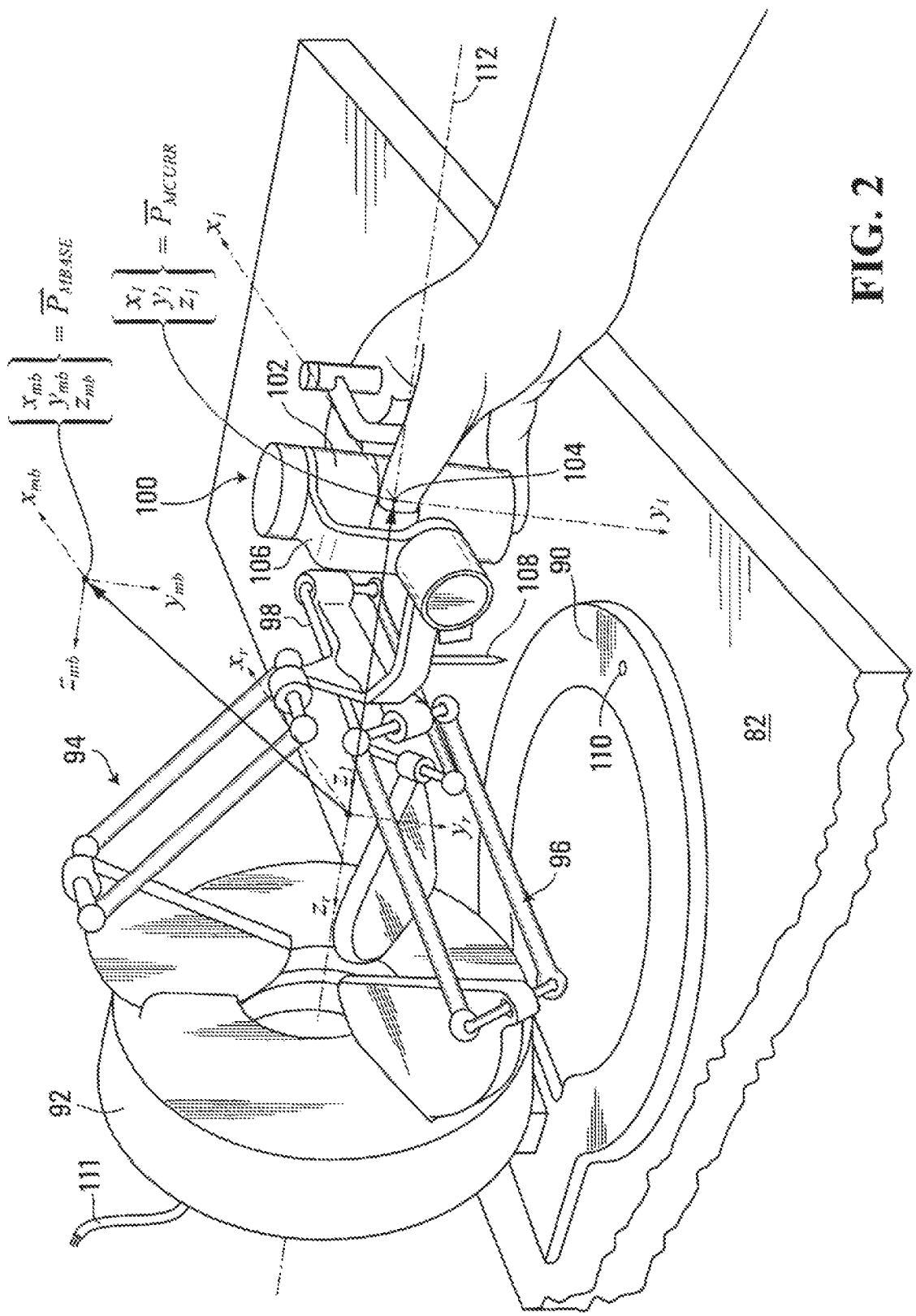
FIG. 2 is an oblique view of an input device of a master subsystem of the laparoscopic surgery system shown in FIG. 1.

Referring to FIG. 2, generally input device 60 includes a base plate 90 that supports a control unit 92 having arms 94, 96, 98 connected to a gimbal-mounted handle 102 that can be grasped by the hand of the operator user and rotated about orthogonal axes $x_1$, $y_1$ and $z_1$ of a first Cartesian reference frame having an origin at a point midway along the axis of a cylinder that forms part of the handle 102. This first Cartesian reference frame may be referred to as the handle reference frame. The origin may be referred to as the handle position 104.

The arms 94, 96, 98 facilitate translational movement of the handle 102 and hence the handle position 104, in space, and confine the movement of the handle position within a volume in space. This volume may be referred to as the handle translational workspace.

The handle 102 is mounted on a gimbal mount 106 having a pin 108. The base plate 90 has a calibration opening 110 for receiving the pin 108. When the pin 108 is received in the opening 110, the input device 60 is in a calibration position that is defined relative to a fixed master Cartesian reference frame comprising orthogonal axes $x_r$, $y_r$, $z_r$ generally in the center of the handle translational workspace. In the embodiment shown, this master reference frame has an $x_r$-$z_r$ plane parallel to the flat surface 82 and a $y_r$ axis perpendicular to the flat surface.

In the embodiment shown, the $z_r$ axis is parallel to the flat surface 82 and is coincident with an axis 112 passing centrally through the control unit 92 so that pushing and pulling the handle 102 toward and away from the center of the control unit 92 along the axis 112 in a direction parallel to the flat surface 82 is movement in the $z_r$ direction.

The control unit 92 has sensors (not shown) that sense the positions of the arms 94, 96, 98 and the rotation of the handle 102 and produces signals representing the handle position 104 (i.e. the center of the handle 102) in the workspace and the rotational orientation of the handle 102 relative to the fixed master reference frame $x_r$, $y_r$, $z_r$. In this embodiment, these position and orientation signals are transmitted on wires 111 of a USB bus to the master apparatus 64. More particularly, the control unit 92 produces current handle position signals and current handle orientation signals that represent the current position and orientation of the handle 102 by a current handle position vector $\bar{P}_{MCURR}$ and a current handle rotation matrix $R_{MCURR}$, relative to the fixed master reference frame $x_r$, $y_r$, $z_r$.

For example, the current handle position vector $\bar{P}_{MCURR}$ is a vector $$\begin{Bmatrix} x_1 \\ y_1 \\ z_1 \end{Bmatrix},$$

where $x_1$, $y_1$, and $z_1$ represent coordinates of the handle position 104 within the handle workspace relative to the fixed master reference frame, $x_r$, $y_r$, $z_r$.

The current handle rotation matrix $R_{MCURR}$ is a 3×3 matrix $$\begin{bmatrix} x_{1x} & y_{1x} & z_{1x} \\ x_{1y} & y_{1y} & z_{1y} \\ x_{1z} & y_{1z} & z_{1z} \end{bmatrix},$$

where the columns of the matrix represent the axes of the handle reference frame $x_1$, $y_1$, $z_1$ written in the fixed master reference frame $x_r$, $y_r$, $z_r$. $R_{MCURR}$ thus defines the current rotational orientation of the handle 102 in the handle translational workspace, relative to the $x_r$, $y_r$, $z_r$ master reference frame.

The current handle position vector $\vec{P}_{MCURR}$ and current handle rotation matrix $R_{MCURR}$ are transmitted in the current handle position and orientation signals on wires 111 of the USB bus, for example, to the master apparatus 64 in FIG. 1.

In addition, in the embodiment shown, referring to FIG. 1, the master apparatus 64 is coupled to a footswitch 170 actuable by the operator (surgeon) to provide a binary enablement signal to the master apparatus 64. When the footswitch 170 is not activated, i.e. not depressed, the enablement signal is in an active state and when the footswitch 170 is depressed the enablement signal is in an inactive state. The footswitch 170 thus controls the state of the enablement signal. As will be seen below, the enablement signal allows the user to cause the master apparatus 64 to selectively enable and disable movement of the end effectors in response to movement of the handles 102.

Figure 7:
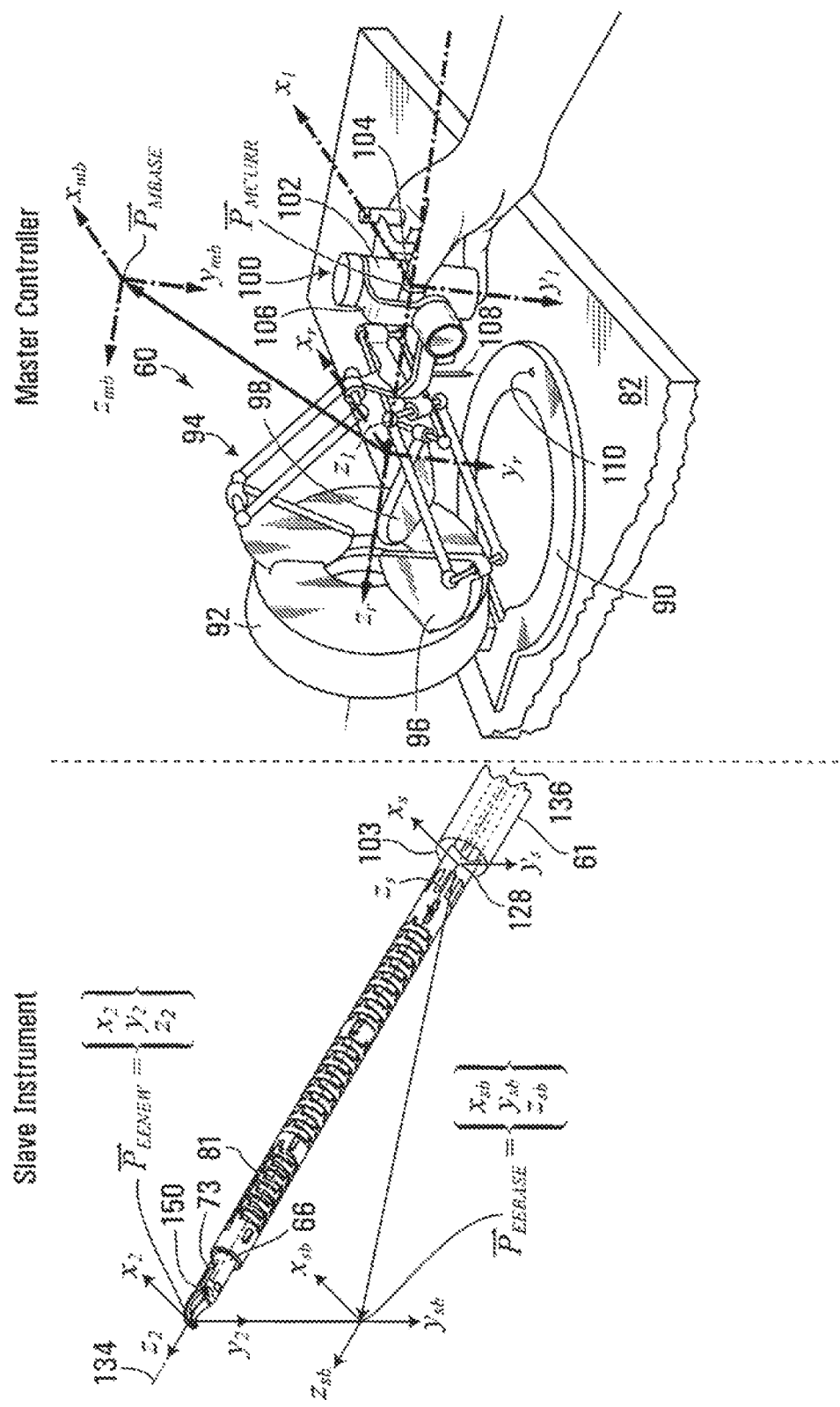
FIG. 7 is an oblique view of the input device shown in FIG. 2 and the tool positioning device shown in FIG. 4 showing relationships between base axes of the input device and the end effector.

Referring now to FIG. 7, the end effector 73 and related structures are described. The fixed slave reference frame has axes $x_s$, $y_s$ and $z_s$ which intersect at a point referred to as the slave fixed base position 128, lying on the longitudinal axis 136 of the insertion tube 61 and contained in a plane perpendicular to the longitudinal axis 136 and containing a distal edge 103 of the insertion tube 61. The $z_s$ axis is coincident with the longitudinal axis 136 of the insertion tube 61. The $x_s$-$z_s$ plane thus contains the longitudinal axis 136 of the insertion tube 61 and the $x_s$ and $y_s$ axes define a plane perpendicular to the longitudinal axis 136 of the insertion tube 61.

In the embodiment shown, end effector 73 includes a pair of gripper jaws. Orthogonal axes $x_2$, $y_2$ and $z_2$ of an end effector Cartesian reference frame have an origin on the end effector axis, for example, at the intersection at the tip of the gripper jaws of the end effector 73. The origin of the end effector reference frame may be referred to as the end effector position 150 relative to the fixed slave reference frame $x_s$, $y_s$, $z_s$. Due to the mobility of the tool positioning device 81 and the mobility of the end effector 73 itself, the end effector position 150 can be placed at discrete positions within a volume in space. This volume may be referred to as the end effector translational workspace.

Figure 3:
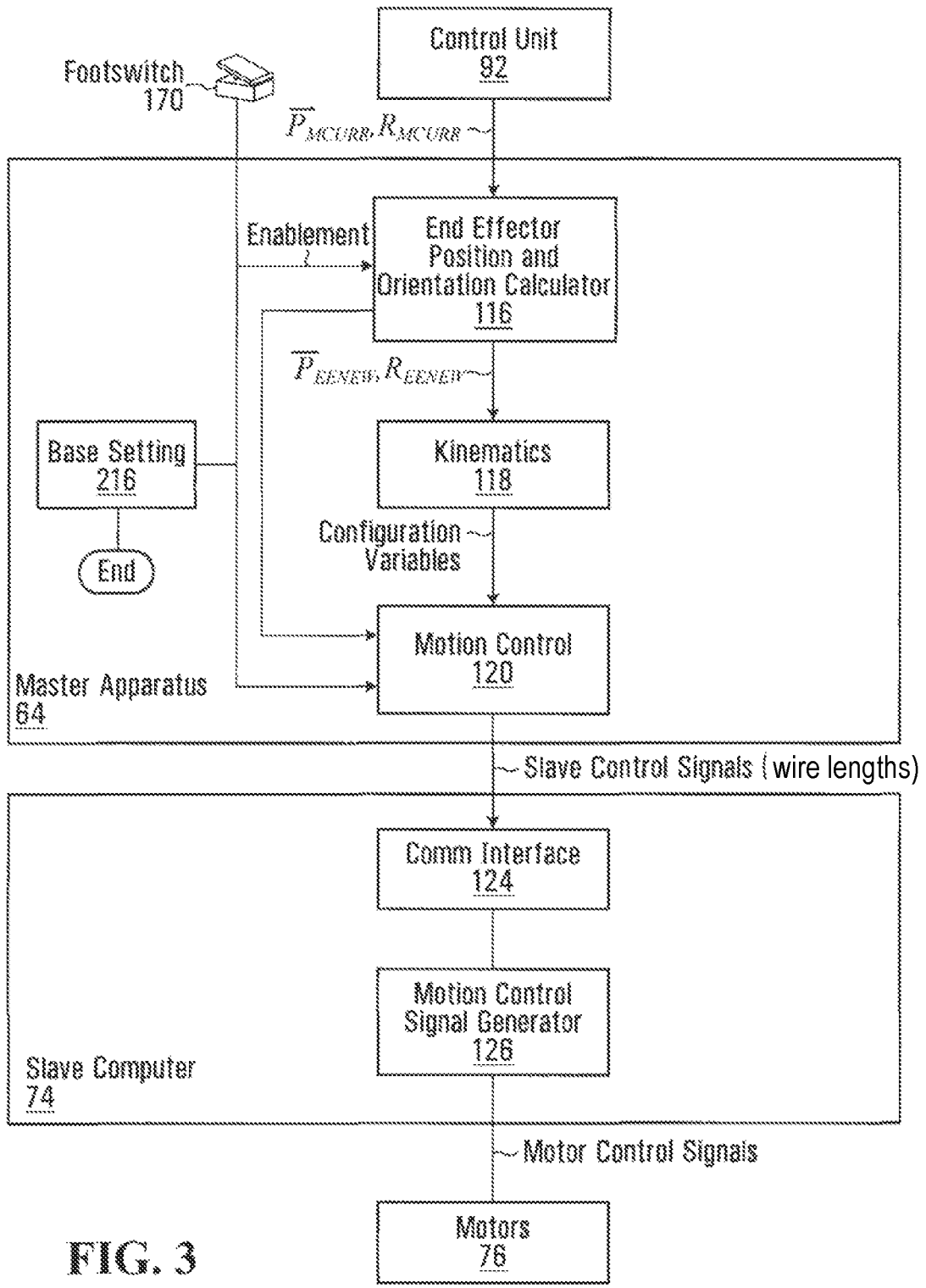
FIG. 3 is a block diagram illustrating certain functionality and certain signals produced and used by the system shown in FIG. 1.

New end effector positions and end effector orientations are calculated by an end effector position and orientation calculation block 116 encoded in the master apparatus 64 shown in FIG. 3, in response to the current handle position signals $\vec{P}_{MCURR}$ and current handle orientation signals $R_{MCURR}$ and are represented by a new end effector position vector $\vec{P}_{EENEW}$ and a new end effector rotation matrix $R_{EENEW}$, relative to the $x_s$, $y_s$, $z_s$ fixed slave reference frame.

For example, the new end effector position vector $\vec{P}_{EENEW}$ is a vector $$\begin{Bmatrix} x_2 \\ y_2 \\ z_2 \end{Bmatrix},$$

where $x_2$, $y_2$, and $z_2$ represent coordinates of the end effector position 150 within the end effector translational workspace relative to the $x_s$, $y_s$, $z_s$ fixed slave reference frame.

The end effector rotation matrix $R_{EENEW}$ is a 3×3 matrix $$\begin{bmatrix} x_{2x} & y_{2x} & z_{2x} \\ x_{2y} & y_{2y} & z_{2y} \\ x_{2z} & y_{2z} & z_{2z} \end{bmatrix},$$

where the columns of the $R_{EENEW}$ matrix represent the axes of the end effector reference frame $x_2$, $y_2$, $z_2$ written in the fixed slave reference frame $x_s$, $y_s$, $z_s$. $R_{EENEW}$ thus defines a new orientation of the end effector 73 in the end effector translational workspace, relative to the $x_s$, $y_s$, $z_s$ reference frame.

Referring back to FIG. 1, in the embodiment shown, the master apparatus 64 is controlled by program codes stored on a non-transitory computer readable medium such as a disk drive 114. The codes direct the master apparatus 64 to perform various functions. Referring to FIGS. 1 and 3, these functions may be grouped into categories and expressed as functional blocks of code including an end effector position and orientation calculation block 116, a kinematics block 118, a motion control block 120, and a base setting block 216, all stored on the disk drive 114 of the master apparatus 64. For ease of description, these blocks are shown as functional blocks within the master apparatus 64 in FIG. 3. These functional blocks are executed separately but in the same manner for each input device 58 and 60. The execution of these functional blocks for only input device 60 and end effector 73 will be described, it being understood they are separately executed in the same way for input device 58 and end effector 71 to achieve control of end effectors 73 and 71 by right and left hands respectively of the operator.

Generally, the end effector position and orientation calculation block 116 includes codes that direct the master apparatus 64 to produce the new end effector position and orientation signals, referred to herein as $\vec{P}_{EENEW}$ and $R_{EENEW}$ respectively.

The kinematics block 118 includes codes that direct the master apparatus 64 to produce configuration variables in response to the newly calculated end effector position and orientation signals $\vec{P}_{EENEW}$ and $R_{EENEW}$.

The motion control block 120 includes codes that direct the master apparatus 64 to produce the slave control signals, in response to the configuration variables.

The base setting block 216 is executed asynchronously, whenever the enablement signal transitions from an inactive state to an active state, such as when the user releases the footswitch 170. The base setting block 216 directs the master apparatus 64 to set new reference positions and orientations for the handle 102 and end effector 73, respectively as will be described below.

Referring back to FIG. 1, in the embodiment shown, the slave control signals represent wire length values indicating how much certain wires of a given tool positioning device 81 of the slave subsystem 54 must be extended or retracted to cause the end effector 73 of the tool 67 to be positioned and rotated in a manner determined by positioning and rotating the corresponding input device 60.

Referring to FIGS. 1 and 3, the slave control signals representing the wire length values are transmitted to the slave computer 74, which has its own computer readable medium encoded with a communication interface block 124 including codes for directing the slave computer to receive the slave control signals from the master apparatus 64. The computer readable medium is also encoded with a motor control signal generator block 126 including codes for causing the slave computer 74 to generate motor control signals for controlling the motors 76 on the tool controller 78 to extend and retract the wires controlling the attached tool positioning device 81 according to the wire length values represented by the slave control signals from the master apparatus 64.

The kinematics block 118 receives newly calculated end effector position and orientation signals $\vec{P}_{EENEW}$ and $R_{EENEW}$ each time the end effector position and orientation calculation block 116 is executed. In response, the kinematics block 118 produces the configuration variables described below.

Figure 4:
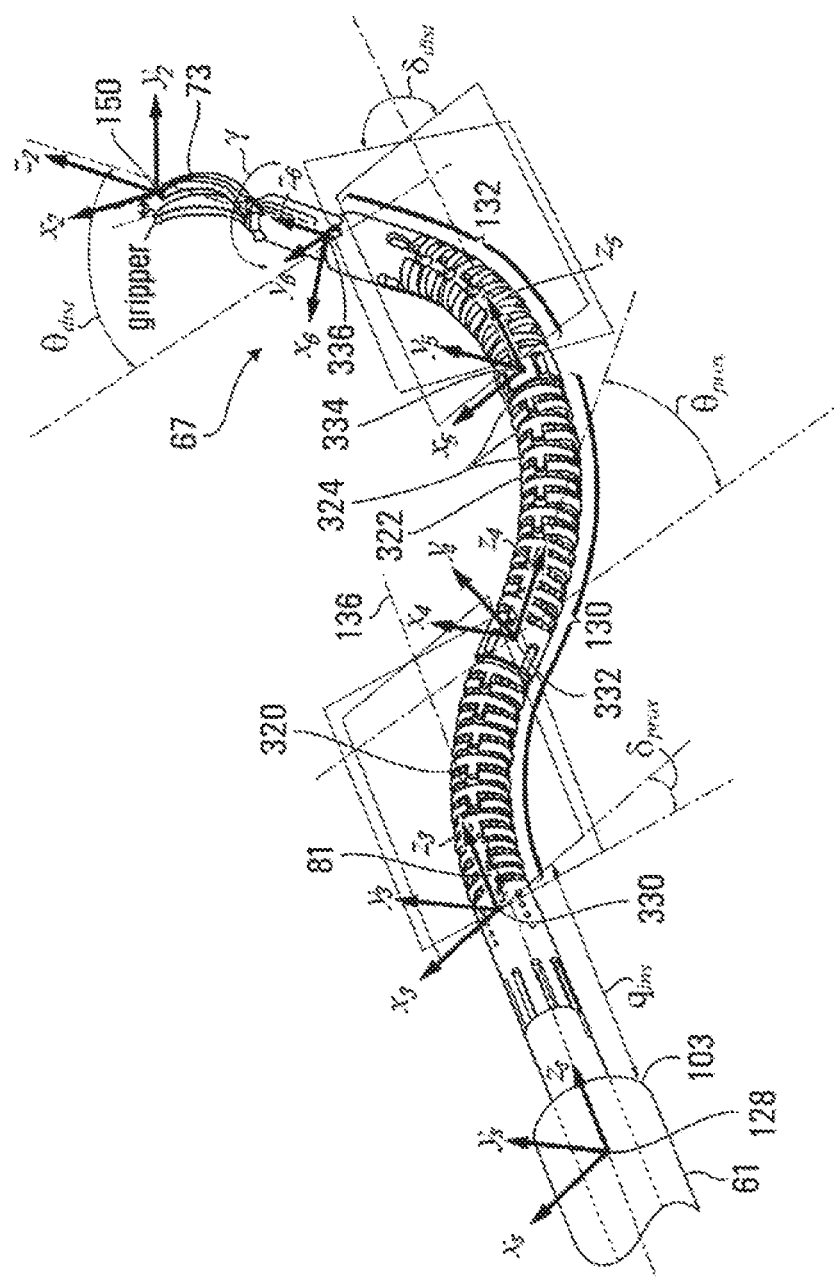
FIG. 4 is an oblique view of a tool positioning device with a tool in the form of an end effector held thereby, in an insertion tube of the laparoscopic surgery system shown in FIG. 1.

Referring to FIGS. 3 and 4, generally, the codes in the kinematics block 118 direct the master apparatus 64 to calculate values for the above configuration variables in response to the end effector position and rotation signals $\vec{P}_{EENEW}$ and $R_{EENEW}$ produced by the end effector position and orientation calculation block 116 and these calculated configuration values generally define a tool positioning device pose required to position end effector 73 at a desired location and at a desired orientation in the end effector translational workspace.

Referring to FIG. 4, the tool positioning device 81 has a first articulated segment 130, referred to as an s-segment and a second articulated segment 132 referred to as a distal segment. The segments 130 and 132 each include a plurality of "vertebra" 324. The s-segment 130 begins at a distance from the insertion tube 61, referred to as the insertion distance $q_{ins}$, which is the distance between the fixed slave base position 128 defined as the origin of the slave fixed base reference frame $x_s$, $y_s$, $z_s$ and a first position 330 at the origin of a first position reference frame $x_3$, $y_3$, and $z_3$. The insertion distance $q_{ins}$ represents an unbendable portion of the tool positioning device 81 that extends out of the end of the insertion tube 61. In the embodiment shown, the insertion distance $q_{ins}$ may be about 10-20 mm, for example. In other embodiments, the insertion distance $q_{ins}$ may be longer or shorter, varying from 0-100 mm, for example.

The s-segment 130 extends from the first position 330 to a third position 334 defined as an origin of a third reference frame having axes $x_5$, $y_5$, and $z_5$ and is capable of assuming a smooth S-shape when control wires (not shown) inside the s-segment 130 are pushed and pulled. The s-segment 130 has a mid-point at a second position 332, defined as the origin of a second position reference frame having axes $x_4$, $y_4$, $z_4$. The s-segment 130 has a length $L_1$, which in the embodiment shown may be about 65 mm, for example.

The distal segment 132 extends from the third position 334 to a fourth position 336 defined as an origin of a fourth reference frame having axes $x_6$, $y_6$, $z_6$. The distal segment 132 has a length $L_2$, which in the embodiment shown may be about 23 mm, for example.

The tool 67 also has an end effector length, which in the embodiment shown is a gripper length $L_3$ that extends from the fourth position 336 to the end effector position 150 defined as the origin of axes $x_2$, $y_2$, and $z_2$. The gripper length $L_3$, in this embodiment, may be about 25 mm, for example. The slave base position 128, first position 330, second position 332, third position 334, fourth position 336 and end effector position 150 may collectively be referred to as tool reference positions.

As explained in PCT/CA2013/001076, hereby incorporated herein by reference in its entirety, by pushing and pulling on certain control wires inside the tool positioning devices 79 and 81, the s-segment 130 can be bent into any of various degrees of an S-shape, from straight as shown in FIG. 7 to a partial S-shape as shown in FIG. 4 to a full S-shape. The s-segment 130 is sectional in that it has a first section 320 and a second section 322 on opposite sides of the second position 332. The first and second sections 320 and 322 lie in a first bend plane containing the first position 330, second position 332, and third position 334. The first bend plane is at an angle $\delta_{prox}$ to the $x_s$-$z_s$ plane of the fixed slave reference frame. The first section 320 and second section 322 are bent in the first bend plane through opposite but equal angles $\theta_{prox}$ such that no matter the angle $\theta_{prox}$ or the bend plane angle $\delta_{prox}$, the $z_s$ axis of the third position 334 is always parallel to and aligned in the same direction as the $z_s$ axis of the fixed slave base position 128. Thus, by pushing and pulling on the control wires within the tool positioning device 81, the third position 334 can be placed at any of a number of discrete positions within a cylindrical volume in space. This volume may be referred to as the s-segment workspace.

In addition, the distal segment 132 lies in a second bend plane containing the third position 334 and the fourth position 336. The second bend plane is at an angle $\delta_{dist}$ to the $x_s$-$z_s$ plane of the fixed slave reference frame. The distal segment 132 is bent in the second bend plane at an angle $\theta_{dist}$. Thus, by pushing and pulling the control wires within the tool positioning device 81, the fourth position 336 can be placed within another volume in space. This volume may be referred to as the distal workspace. The combination of the s-segment workspace plus the distal workspace can be referred to as the tool positioning device workspace, as this represents the total possible movement of the tools 66 and 67 as effected by the respective tool positioning devices 79 and 81.

The distance between the fourth position 336 and the end effector position 150 is the distance between the movable portion of the distal segment 132 and the tip of the gripper end effector 73 in the embodiment shown, i.e. the length $L_3$. Generally, the portion of the gripper between the fourth position 336 and the end effector position 150 ($L_3$) will be unbendable.

In the embodiment shown, the end effector 73 is a gripper jaw tool that is rotatable about the $z_2$ axis in the $x_2$-$y_2$ plane of the end effector reference frame, the angle of rotation being represented by an angle $\gamma$ relative to the positive $x_2$ axis. Finally, the gripper jaws may be at any of varying degrees of openness from fully closed to fully open (as limited by the hinge). The varying degrees of openness may be defined as the "gripper".

In summary therefore, the configuration variables provided by the kinematic block 118 codes are as follows:

- $q_{ins}$: represents a distance from the slave base position 128 defined by axes $x_s$, $y_s$, and $z_s$ to the first position 330 defined by axes $x_3$, $y_3$ and $z_3$ where the s-segment 130 of the tool positioning device 81 begins;
- $\delta_{prox}$: represents a first bend plane in which the s-segment 130 is bent relative to the $x_s$-$y_s$ plane of the fixed slave reference frame;
- $\theta_{prox}$: represents an angle at which the first and second sections 320 and 322 of the s-segment 130 is bent in the first bend plane;
- $\theta_{dist}$: represents a second bend plane in which the distal segment 132 is bent relative to the $x_s$-$y_s$ plane of the fixed slave reference frame;
- $\theta_{dist}$: represents an angle through which the distal segment 132 is bent in the second bend;
- γ: represents a rotation of the end effector 73 about axis $z_2$; and
- Gripper: represents a degree of openness of the gripper jaws of the end effector 73. (This is a value which is calculated in direct proportion to a signal produced by an actuator (not shown) on the handle 102 indicative of an amount of pressure the operator exerts by squeezing the handle).

To calculate the configuration variables, it will first be recalled that the end effector rotation matrix $R_{EENEW}$ is a 3×3 matrix:

$$\begin{bmatrix} x_{2x} & y_{2x} & z_{2x} \\ x_{2y} & y_{2y} & z_{2y} \\ x_{2z} & y_{2z} & z_{2z} \end{bmatrix}.$$

Since the last column of $R_{EENEW}$ is the z-axis of the end effector reference frame written relative to the fixed slave reference frame $x_s$, $y_s$ and $z_s$, the values $\theta_{dist}$, $\theta_{dist}$, and γ associated with the distal segment 132 can be calculated according to the relations:

$$\theta_{dist} = \frac{\pi}{2} - \text{atan2}\left(\sqrt{z_{2x}^2 + z_{2y}^2}, z_{2z}\right) \tag{2}$$

$$\delta_{dist} = -\text{atan2}(z_{2y}, z_{2x}) \tag{3}$$

If $|\delta_{dist}| > \frac{\pi}{2}$ $$\gamma = \text{a tan } 2(-y_{2z}, y_{2z}) - \delta_{dist} + \pi \tag{4a}$$

else $$\gamma = \text{a tan } 2(y_{2z}, -x_{2z}) - \delta_{dist} \tag{4b}$$

These values can then be used to compute the locations of the third position 334, the fourth position 336, and the end effector position 150 relative to the fixed slave base position 128. The locations may be expressed in terms of vectors $\vec{p}_{3/s}$ from the fixed slave base position 128 to the first position 330, $\vec{p}_{4/3}$ from the third position 334 to the fourth position 336, and $\vec{p}_{5/4}$ from the fourth position 336 to the end effector position 150. $\vec{p}_{3/s}$ is then calculated from $\vec{p}_{EENEW}$ as follows:

$$\vec{p}_{3/s} = \vec{p}_{EENEW} - \vec{p}_{4/3} - \vec{p}_{5/4}, \tag{5}$$

where:

$$\vec{p}_{4/3} \cdot \vec{i} = \frac{-L_2 \cos\delta_{dist}(\sin\theta_{dist} - 1)}{\frac{\pi}{2} - \theta_{dist}} \tag{6a}$$

$$\vec{p}_{4/3} \cdot \vec{j} = \frac{L_2 \sin\delta_{dist}(\sin\theta_{dist} - 1)}{\frac{\pi}{2} - \theta_{dist}} \tag{6b}$$

$$\vec{p}_{4/3} \cdot \vec{k} = \frac{L_2 \cos(\theta_{dist})}{\frac{\pi}{2} - \theta_{dist}} \tag{6c}$$

$$\vec{p}_{5/4} \cdot \vec{i} = L_3 \cos(\delta_{dist}) \cos(\theta_{dist}) \tag{7a}$$

$$\vec{p}_{5/4} \cdot \vec{j} = -L_3 \sin(\delta_{dist}) \cos(\theta_{dist}) \tag{7b}$$

$$\vec{p}_{5/4} \cdot \vec{k} = L_3 \sin(\theta_{dist}), \tag{7c}$$

where:
- $\vec{i}$ is a unit vector in the x direction;
- $\vec{j}$ is a unit vector in the y direction; and
- $\vec{k}$ is a unit vector in the z direction.

Once the vector from the fixed slave base position 128 to the third position 334 ($\vec{p}_{3/s}$) is known, the configuration variables, $\delta_{prox}$ and $\theta_{prox}$, for the s-segment 130 can be found. The configuration variable $\delta_{prox}$ associated with the s-segment 130 is calculated by solving the following two equations for $\delta_{prox}$:

$$\vec{p}_{3/s} \cdot \vec{i} = \frac{-L_1 \cos\delta_{prox}(\sin\theta_{prox} - 1)}{\frac{\pi}{2} - \theta_{prox}} \tag{8a}$$

$$\vec{p}_{3/s} \cdot \vec{j} = \frac{L_1 \sin\delta_{prox}(\sin\theta_{prox} - 1)}{\frac{\pi}{2} - \theta_{prox}}. \tag{8b}$$

The ratio of (8b) and (8a) gives $$\delta_{prox} = \text{a tan } 2(-\vec{p}_{3/s} \cdot \vec{j}, \vec{p}_{3/s} \cdot \vec{i}) \tag{9}$$

where $\vec{i}$ and $\vec{j}$ are unit vectors in the x and y directions respectively.

A closed form solution cannot be found for $\theta_{prox}$, thus $\theta_{prox}$ must be found with a numerical equation solution to either of equations (8a) or (8b). A Newton-Raphson method, being a method for iteratively approximating successively better roots of a real-valued function, may be employed, for example. The Newton-Raphson method can be implemented using the following equations:

$$f(\theta_{prox}) = \frac{L_1}{\frac{\pi}{2} - \theta_{prox}} \cos\delta_{prox}(1 - \sin\theta_{prox}) - \vec{p}_{3/s} \cdot \vec{i} = 0, \tag{10}$$

where $\vec{i}$ is the unit vector in the x direction.

The equation (10) is equation (8a) rewritten in the form $f(\theta_{prox})=0$. The Newton-Raphson method tends to converge very quickly because in the range $0<\theta_{prox}<\pi$, the function has a large radius of curvature and has no local stationary points. Following the Newton-Raphson method, successive improved estimates of $\theta_{prox}$ can be made iteratively to satisfy equation (10) using the following relationship:

$$\theta_{n+1} = \theta_n - \frac{f(\theta_n)}{f'(\theta_n)} \tag{11}$$

Finally, upon determination of $\theta_{prox}$, the following equation can be used to find $q_{ins}$, $$q_{ins} = -\vec{p}_{3/s} \cdot \vec{k} - \frac{L_1 \cos\theta_{prox}}{\frac{\pi}{2} - \theta_{prox}}, \tag{12}$$

where:
$\vec{k}$ is the unit vector in the z direction;
$\vec{p}_{3/s} \cdot \vec{k}$ is the dot product of the vector $\vec{p}_{3/s}$ and the unit vector $\vec{k}$.

Figure 6:
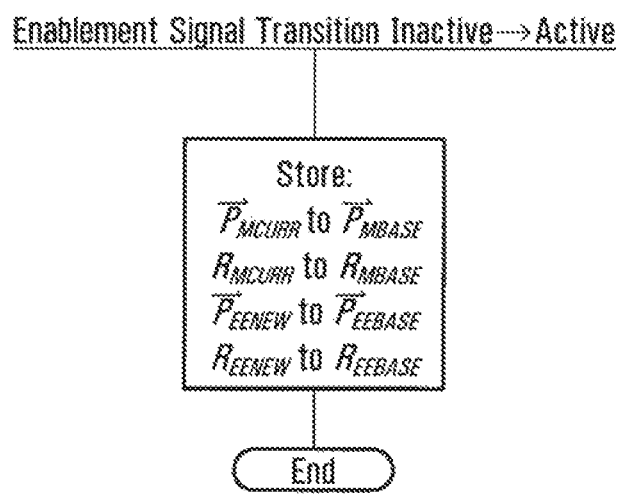
FIG. 6 is a block diagram of a storage routine executed by the master apparatus in response to detection of a signal transition of an enablement signal produced in response to user input.

The codes in the kinematics block 118 shown in FIG. 6 direct the master apparatus 64 to calculate values for the above configuration variables in response to the end effector position and orientation signals $\vec{P}_{EENEW}$ and $R_{EENEW}$ produced by the end effector position and orientation calculation block 116 and these calculated configuration variables generally define a tool positioning device pose required to position the end effector 73 at a desired location and at a desired orientation in the end effector workspace.

It will be appreciated that configuration variables are produced for each end effector 71 and 73 and therefore in the embodiment shown, two sets of configuration variables which will be referred to as left and right configuration variables respectively are produced and forwarded or otherwise made available to the motion control block 120.

Figure 5:
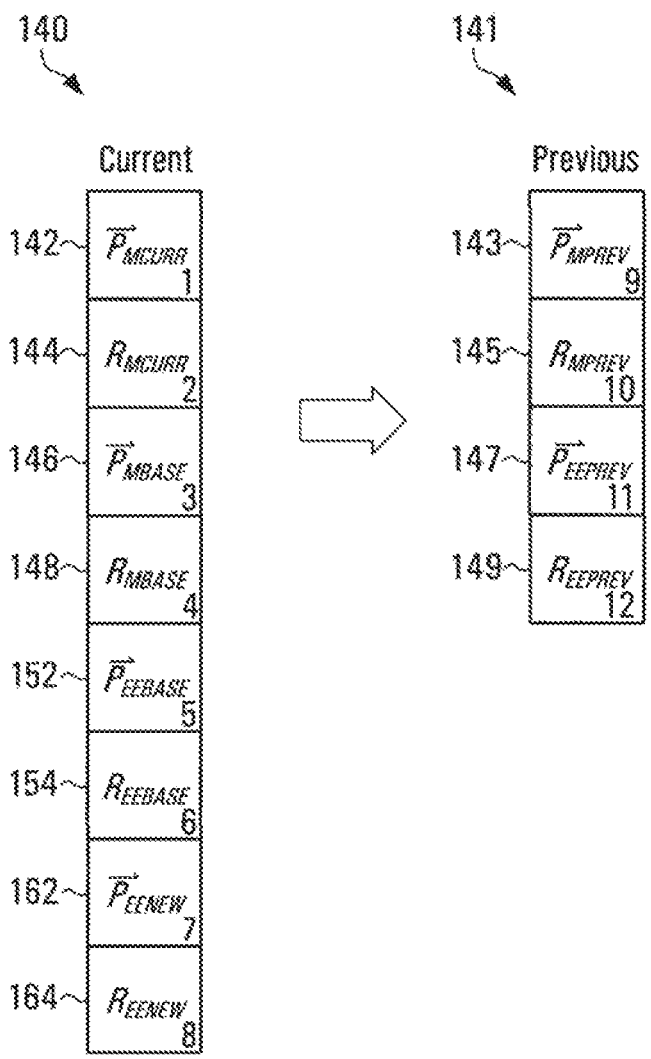
FIG. 5 is a schematic representation of current and previous value buffers maintained by a master apparatus of the laparoscopic surgery system shown in FIG. 1 and updated according to the functions shown in FIGS. 6, 8A and 8B.

Referring to FIG. 5, the master apparatus 64 queries the control unit 92 for the current handle position vector $\vec{P}_{MCURR}$ and current handle rotation matrix $R_{MCURR}$ periodically, at a sample rate of about 1 kHz. These values are stored by the master apparatus 64 in a first "current" buffer 140 having a first store 142 storing the three values representing the currently acquired handle position vector $\vec{P}_{MCURR}$ and a second store 144 storing the nine values representing the acquired handle rotation matrix $R_{MCURR}$.

Referring to FIGS. 2 and 5, the master apparatus 64 also stores values $x_{mb}$, $y_{mb}$, $z_{mb}$ representing a definable master base position represented by a base position vector $\vec{P}_{MBASE}$ in a third store 146 and stores values representing a definable master base rotation matrix $R_{MBASE}$ in a fourth store 148. The master apparatus 64 initially causes the definable master base position vector $\vec{P}_{MBASE}$ to be set equal to the current handle position vector $\vec{P}_{MCURR}$ on startup of the system and causes the definable master base rotation matrix $R_{MBASE}$ to define an orientation that is the same as the orientation defined by the current handle rotation matrix $R_{MCURR}$ associated with the current handle rotation, on startup of the system.

Initially, therefore:

$\vec{P}_{MBASE} = \vec{P}_{MCURR}$; and
$R_{MBASE} = R_{MCURR}$.

In other words, the master base reference frame and the handle reference frame coincide at startup.

Thereafter, the master base position vector $\vec{P}_{MBASE}$ and the master base rotation matrix $R_{MBASE}$ are maintained at the same values as on startup until the enablement signal is activated, such as by inactivation of the footswitch (170 in FIGS. 1 and 3), which causes the enablement signal to transition from the inactive state to the active state. In response, the base setting block 216 shown in FIG. 3 and more in detail in FIG. 6 is executed to change the master base position vector $\vec{P}_{MBASE}$ and master base rotation matrix $R_{MBASE}$ to the currently acquired handle position vector $\vec{P}_{MCURR}$ and currently acquired handle orientation matrix $R_{MCURR}$ respectively.

Referring to FIGS. 5 and 7, the master apparatus 64 further stores values $x_{sb}$, $y_{sb}$, $z_{sb}$ representing a definable slave base position vector $\vec{P}_{EEBASE}$ in a fifth store 152 and stores values representing a definable slave base rotation matrix $R_{EEBASE}$ in a sixth store 154. The master apparatus 64 initially causes the definable slave base position vector $\vec{P}_{EEBASE}$ to be set equal to the new end effector position vector $\vec{P}_{EENEW}$ and causes the definable slave base rotation matrix $R_{EEBASE}$ to define an orientation that is the same as the orientation defined by the new end effector rotation matrix $R_{EENEW}$ on startup of the system.

Initially, therefore:

$\vec{P}_{EEBASE} = \vec{P}_{EENEW}$; and
$R_{EEBASE} = R_{EENEW}$.

In other words, the slave base reference frame and the end effector reference frame coincide at startup.

The slave base position $\vec{P}_{EEBASE}$ and slave base rotation matrix $R_{EEBASE}$ are maintained at the same values as on startup until the enablement signal is activated such as by inactivation of the footswitch (170 in FIGS. 1 and 3), which causes the enablement signal to transition to the active state. In response, the base setting block 216 in FIG. 6 directs the master apparatus 64 to change the slave base position vector $\vec{P}_{EEBASE}$ and slave base rotation matrix $R_{EEBASE}$ to the newly calculated end effector position vector $\vec{P}_{EENEW}$ and newly calculated end effector rotation matrix $R_{EENEW}$.

Referring to FIGS. 3 and 8A to 8D, the end effector position and orientation calculation block 116 is executed each time a set of new values for $\vec{P}_{MCURR}$ and $R_{MCURR}$ are acquired from the control unit 92. It begins with a first block 161 that directs the master apparatus 64 to check the state of the enablement signal to determine whether it is active or inactive. If the enablement signal is active, then the process continues at block 160 shown in FIG. 8B. Block 160 directs the master apparatus 64 to produce and store, in a seventh store 162 in FIG. 5, values representing the new end effector position vector $\vec{P}_{EENEW}$ and to produce and store, in an eighth store 164 in FIG. 5, values representing the new end effector rotation matrix $R_{EENEW}$.

To produce new end effector position signals $\vec{P}_{EENEW}$ and new end effector orientation signals $R_{EENEW}$ representing a desired end effector position 150 and desired end effector orientation, relative to the slave base position 128 and the slave base rotation, the new end effector position signals $\vec{P}_{EENEW}$ and new end effector orientation signals $R_{EENEW}$ are calculated according to the following relations:

$\vec{P}_{EENEW} = A(\vec{P}_{MCURR} - \vec{P}_{MBASE}) + \vec{P}_{EEBASE}$ and $$R_{EENEW} = R_{EEBASE} R_{MBASE}^{-1} R_{MCURR}$$

Where: $\bar{P}_{EENEW}$ is the new end effector position vector that represents the new desired end effector position 150 of the end effector 73 in the end effector workspace, relative to the slave base reference frame;

A is a scalar value representing a scaling factor in translational motion between the master and the slave;

$\bar{P}_{MCURR}$ is the current representation of the handle position vector stored in the first store 142, the handle position vector being relative to the fixed master reference frame;

$\bar{P}_{MBASE}$ is the last-saved position vector $\bar{P}_{MCURR}$ for the handle 102 that was saved upon the last inactive to active state transition of the enablement signal such as by release of the footswitch 170 or on system initialization or by operation of a control interface by the operator;

$\bar{P}_{EEBASE}$ is the last-saved position vector $\bar{P}_{EENEW}$ for the end effector 73 that was saved upon the last inactive to active state transition of the enablement signal;

$R_{EENEW}$ is the new end effector rotation matrix representing the current orientation of the end effector 73 relative to the slave reference frame;

$R_{EEBASE}$ is the rotation matrix representing the last-saved orientation of the end effector 73 saved upon the last inactive to active state transition of the enablement signal;

$R_{MBASE}^{-1}$ is the inverse of rotation matrix $R_{MBASE}$, where $R_{MBASE}$ is a rotation matrix representing the last-saved orientation of the handle 102 saved upon the last inactive to active state transition of the enablement signal;

$R_{MCURR}$ is the currently acquired rotation matrix representing the orientation of the handle 102 relative to the fixed master reference frame.

The following describes how the master apparatus 64 is controlled by the codes in the end effector position and orientation calculation block 116 to effect autonomous alignment of the orientation of the end effector 73 with the handle 102 after clutching and to effect autonomous alignment of the z-axes of the handle 102 and end effector 73 for wrist roll management.

Figure 8A:
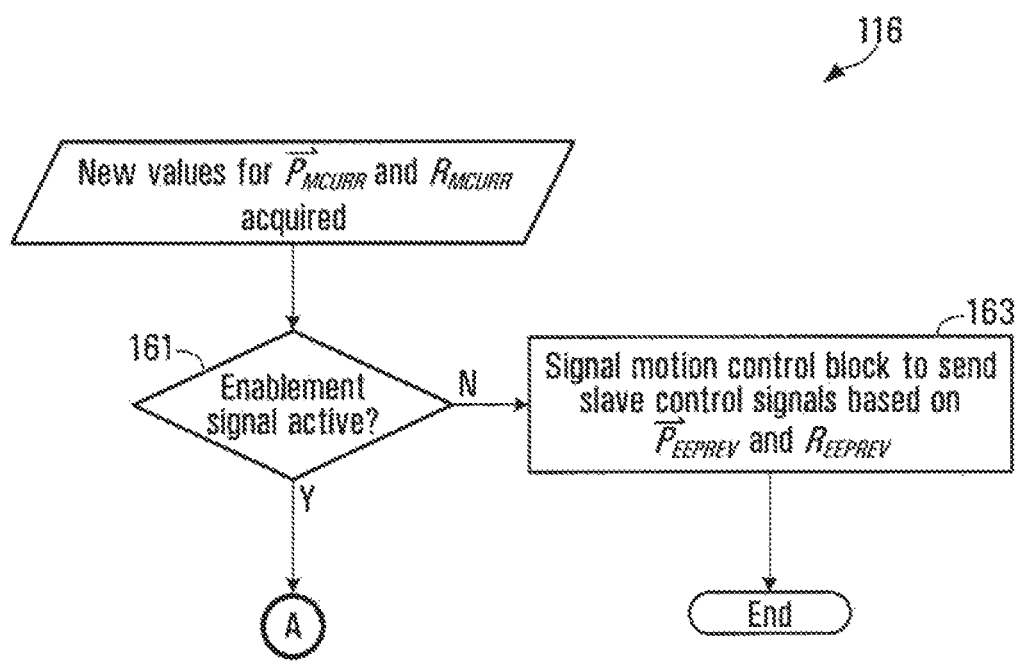
Figure 8B:
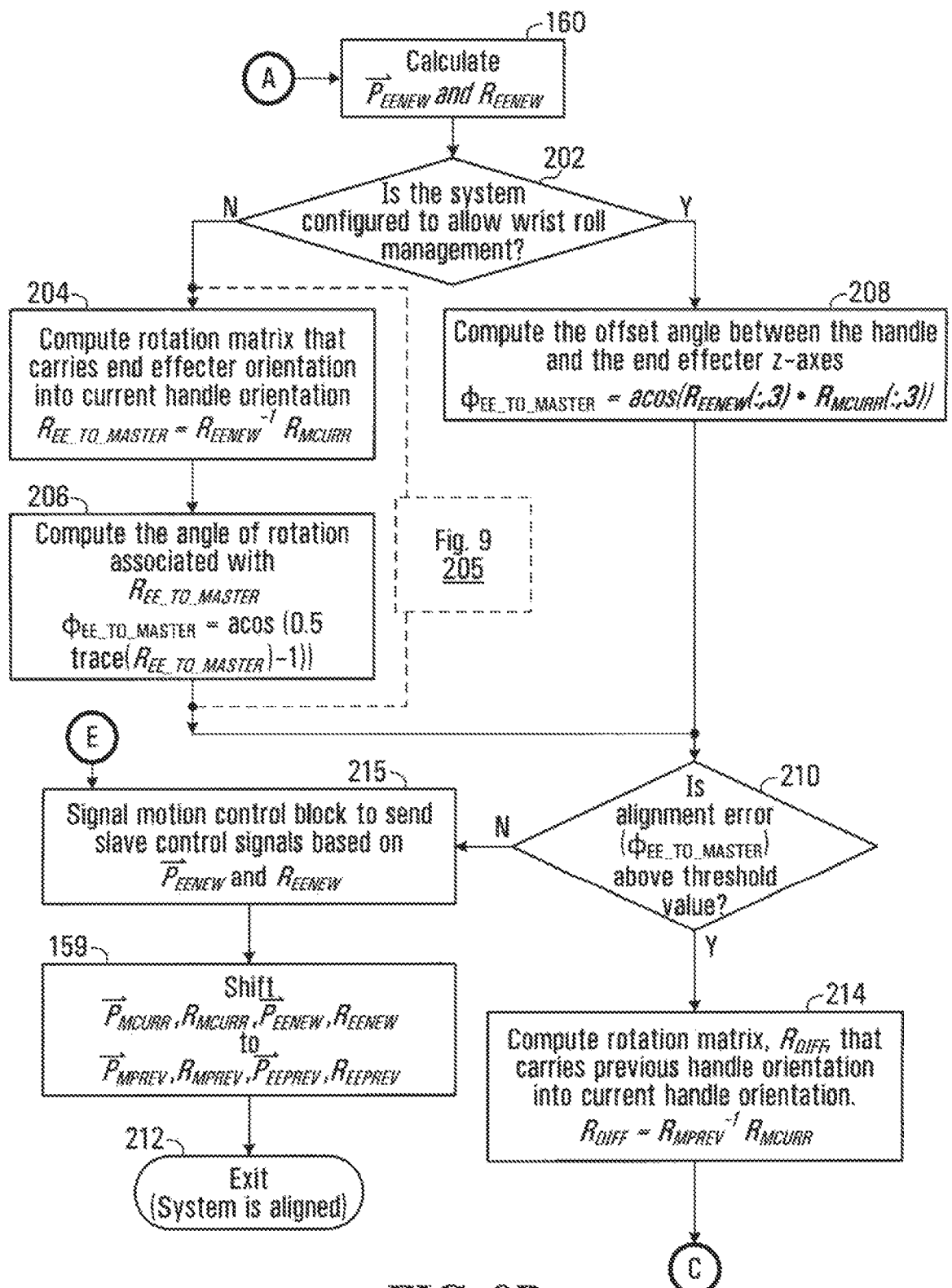

Referring to FIG. 8B, after values representing the desired end effector position and orientation signals $\bar{P}_{EENEW}$ and $R_{EENEW}$ are calculated by the master apparatus 64 executing block 160, the master apparatus 64 is directed to block 202 which directs the master apparatus to determine whether the system 50 is configured to allow wrist roll management. A simple binary wrist roll management signal selectively set by the operator is used to indicate to the master apparatus 64 whether the system 50 is configured to allow wrist roll management or not. If the system is not configured for wrist roll management, block 204 directs the master apparatus 64 to compute a rotation matrix that carries the newly calculated end effector orientation into the current handle orientation ($R_{EE\_TO\_MASTER}$) by the relation:

$$R_{EE\_TO\_MASTER} = R_{EENEW}^{-1} R_{MCURR}$$

Where: $R_{EENEW}^{-1}$ is the inverse matrix of the end effector rotation matrix $R_{EENEW}$ represented by a 3×3 matrix stored in the eighth store 164 in FIG. 3; and $R_{MCURR}$ is the current handle rotation matrix represented by the 3×3 matrix stored in the second store 144 in FIG. 3.

Then, block 206 directs the master apparatus 64 to compute an angle of rotation associated With $R_{EE\_TO\_MASTER}$ ($\Phi_{EE\_TO\_MASTER}$) by the relation:

$$\Phi_{EE\_TO\_MASTER} = a\cos(0.5\,\text{trace}(R_{EE\_TO\_MASTER}) - 1)$$

This angle of rotation ($\Phi_{EE\_TO\_MASTER}$) represents the alignment difference between the orientation of the handle 102 and the newly calculated end effector orientation.

In a special case, applicable to the embodiment described here, it is desirable that to be aligned, only the z-axes of the reference frames described by $R_{EENEW}$ and $R_{MCURR}$ be coincident. In this case the handle 102 and the end effector 73 point in the same direction relative to their respective fixed reference frames ($x_r$, $y_r$, $z_r$ and $x_s$, $y_s$, $z_s$, respectively) and the roll about their z-axis is not considered.

In this special case therefore, blocks 204 and 206 shown in FIG. 8B are replaced with block 205 shown in FIG. 9 which involves the following computation $$\Phi_{EE\_TO\_MASTER} = a\cos(R_{EENEW}(1,3) * R_{M\_CURR}(1,3) + R_{EENEW}(2,3) * R_{M\_CURR}(2,3) + R_{EENEW}(3,3) * R_{M\_CURR}(3,3))$$

Where (i,j) represent matrix row (i) and column (j) indices.

This computation represents the angle obtained from the dot product of the z-axes of the handle reference frame and end effector reference frame.

Referring back to FIG. 8B, alternatively, if at block 202 it is determined that the system is configured to allow wrist roll management, block 208 directs the master apparatus 64 to compute an offset angle between the handle reference frame and the end effector reference frame z-axes ($\Phi_{EE\_TO\_MASTER}$) by the relation:

$$\phi_{EE\_TO\_MASTER} = a\cos\left(\begin{pmatrix} R_{EENEW1,3} \\ R_{EENEW2,3} \\ R_{EENEW3,3} \end{pmatrix} \cdot \begin{pmatrix} R_{MCURR1,3} \\ R_{MCURR2,3} \\ R_{MCURR3,3} \end{pmatrix}\right)$$

After executing either block 206 or block 208, the angle of rotation by which the handle 102 and end effector 73 are out of alignment, i.e. the alignment error, is given by $\Phi_{EE\_TO\_MASTER}$.

The master apparatus 64 is then directed to block 210 which causes it to determine whether the alignment error $\Phi_{EE\_TO\_MASTER}$ meets a criterion, such as being above a threshold value. If the alignment error is not above the threshold value, the current handle orientation $R_{MCURR}$ and new end effector orientation $R_{EENEW}$ are considered to be aligned.

Then, block 215 directs the master apparatus 64 to signal the motion control block 120 of FIG. 3 to indicate that slave control signals based on the newly calculated values for $\bar{P}_{EENEW}$ and $R_{EENEW}$ are to be sent to the slave computer 74. This causes the end effector 73 to assume a position and orientation determined by the current position and current orientation of the handle 102 when the alignment difference meets the criterion.

Block 159 then directs the master apparatus 64 to copy the newly calculated end effector position vector $\bar{P}_{EENEW}$ and end effector rotation matrix $R_{EENEW}$ into an eleventh and twelfth stores 147 and 149 of a previous buffer 141 of FIG. 5. The newly calculated end effector position vector $\bar{P}_{EENEW}$ and newly calculated end effector rotation matrix $R_{EENEW}$ are thus renamed as "previously calculated end effector position vector" $\vec{P}_{EEPREV}$ and "previously calculated end effector rotation matrix" $R_{EEPREV}$. By storing the newly calculated end effector position vector $\vec{P}_{EENEW}$ and newly calculated end effector rotation matrix $R_{EENEW}$, as previously calculated end effector position vector $\vec{P}_{EEPREV}$ and previously calculated end effector rotation matrix $R_{EEPREV}$, a subsequently acquired new end effector position vector $\vec{P}_{EENEW}$ and subsequently acquired new end effector rotation matrix $R_{EENEW}$ can be calculated from the next current handle position vector $\vec{P}_{MCURR}$ and next current handle position matrix $R_{MCURR}$.

The end effector position and orientation calculation block 116 is thus completed, and the calculated $\vec{P}_{EENEW}$ and $R_{EENEW}$ values stored in the seventh and eighth stores 162 and 164 are available for use by the kinematics block 118.

If at block 210 the alignment error is above the threshold value, block 214 directs the master apparatus 64 to produce a rotation matrix that carries the previous handle orientation into current handle orientation ($R_{DIFF}$), according to the relation:

$$R_{DIFF} = R_{MPREV}^{-1} R_{MCURR}$$

Where: $R_{MPREV}^{-1}$ is the inverse of the previous handle rotation matrix stored in the tenth store 145 of FIG. 3; and $R_{MCURR}$ is the current handle rotation matrix stored in the second store 144 of FIG. 3.

Figure 8C:
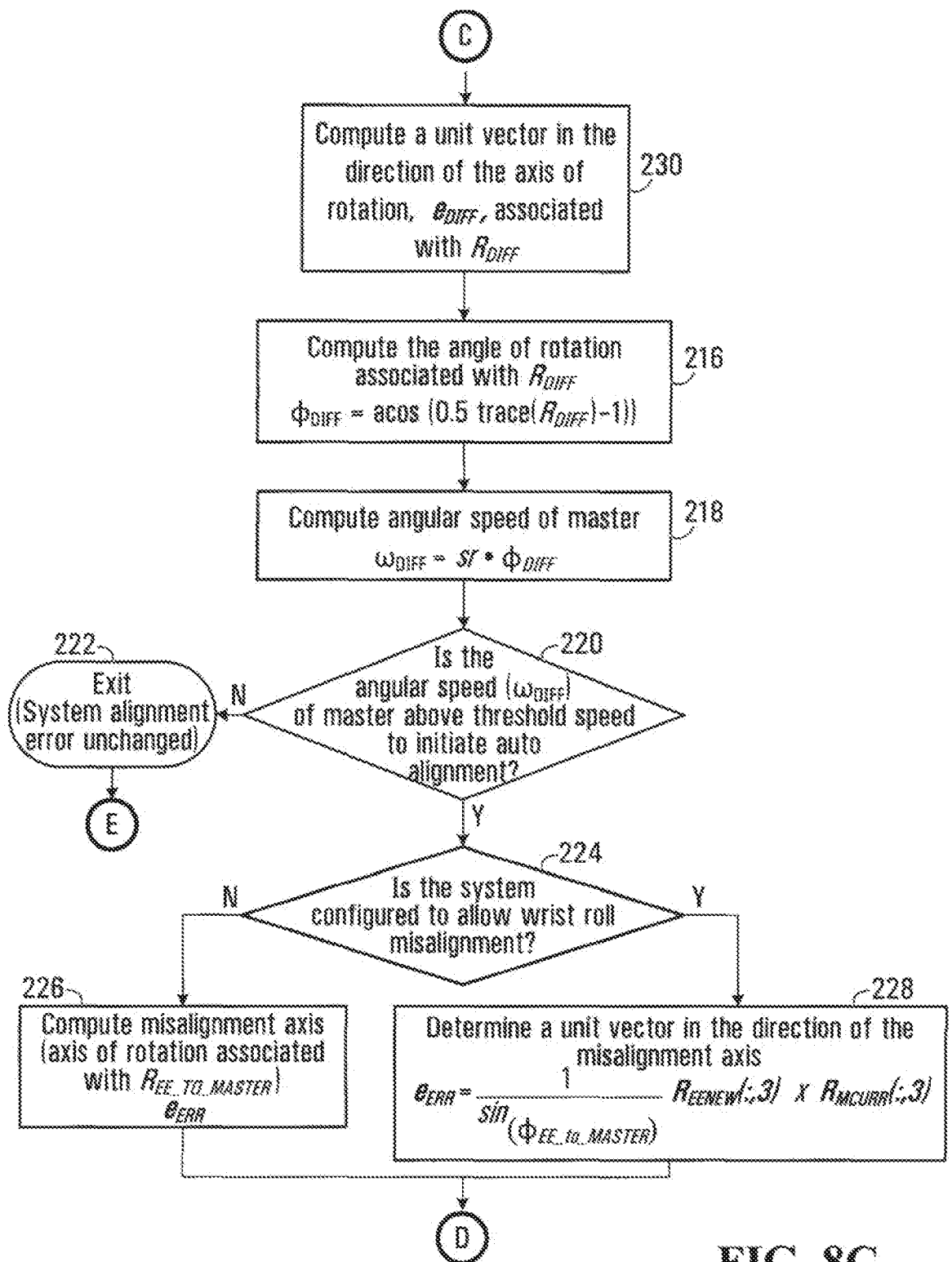

Referring to FIG. 8C, the master apparatus 64 is then directed by block 230 to determine a unit vector in the direction of an axis of rotation ($e_{DIFF}$) associated with $R_{DIFF}$ by the relation:

$$p = 0.5 \begin{Bmatrix} R_{DIFF3,2} - R_{DIFF2,3} \\ R_{DIFF1,3} - R_{DIFF3,1} \\ R_{DIFF2,1} - R_{DIFF1,2} \end{Bmatrix}$$

$$\vec{e}_{DIFF} = \frac{p}{\|p\|}$$

Then, block 216 directs the master computer 64 to compute an angle of rotation ($\Phi_{DIFF}$) associated with $R_{DIFF}$ by the relation:

$$\Phi_{DIFF} = a\cos(0.5\,\text{trace}(R_{DIFF}) - 1)$$

Then, block 218 directs the master computer 64 to compute an angular speed of the rotation ($\omega_{DIFF}$) associated with $R_{DIFF}$ by the relation:

$$\omega_{DIFF} = sr \cdot \Phi_{DIFF}$$

Where: sr=sample rate in Hz at which $\vec{P}_{MCURR}$ and $R_{MCURR}$ values are acquired from the control unit (92).

Then, block 220 directs the master apparatus 64 to determine whether the angular speed WDIFF meets a second criterion such as being above a threshold speed to initiate auto alignment. (This may avoid any automated motion when the user is performing slow fine movements that may be undesirable.)

If not, the master apparatus 64 is directed to block 222 which corresponds to location "E" on FIG. 8B to execute blocks 215 and 159 and then exit the end effector position and orientation calculation block 116. The saved 15 $\vec{P}_{EENEW}$ and $R_{EENEW}$ values in the seventh and eighth stores 162 and 164 of FIG. 3 are then available for use by the kinematics block 118.

If at block 220 the angular speed $\omega_{DIFF}$ is above the threshold speed, block 224 directs the master computer 64 to determine whether the system is configured to allow wrist roll misalignment by reading the status of the wrist roll management signal set by the operator. If the wrist roll management signal is not active, block 226 directs the master apparatus 64 to determine a misalignment axis $e_{ERR}$, i.e. the axis of rotation associated with $R_{EE\_TO\_MASTER}$ by the relation $$q = 0.5 \begin{Bmatrix} R_{EE\_TO\_MASTER3,2} - R_{EE\_TO\_MASTER2,3} \\ R_{EE\_TO\_MASTER1,3} - R_{EE\_TO\_MASTER3,1} \\ R_{EE\_TO\_MASTER2,1} - R_{EE\_TO\_MASTER1,2} \end{Bmatrix}$$

$$\vec{e}_{ERR} = \frac{q}{\|q\|}$$

Alternatively, if the system is configured to allow wrist roll misalignment, block 228 directs the master apparatus 64 to determine a unit vector in the direction of the misalignment axis $e_{ERR}$ by the relation:

$$e_{ERR} = \frac{1}{\sin(\phi_{EE\_TO\_MASTER})} \begin{Bmatrix} R_{EENEW1,3} \\ R_{EENEW2,3} \\ R_{EENEW3,3} \end{Bmatrix} \times \begin{Bmatrix} R_{MCURR1,3} \\ R_{MCURR2,3} \\ R_{MCURR3,3} \end{Bmatrix}$$

Figure 8D:
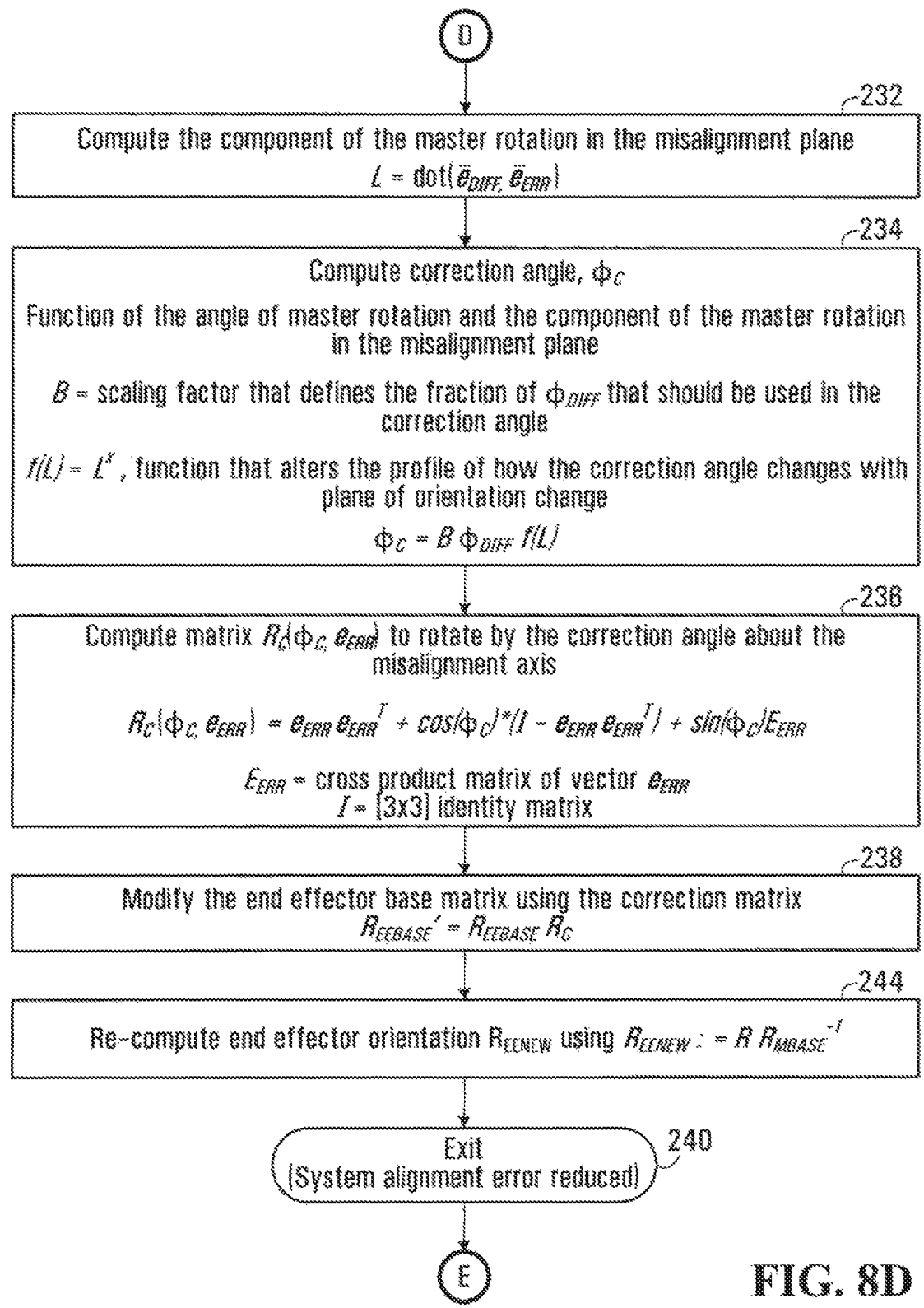

Now referring to FIG. 8D, block 232 directs the master apparatus 64 to compute the component of the handle rotation in the misalignment plane L by the relation:

$$L = |\vec{e}_{DIFF} \cdot \vec{e}_{ERR}|$$

Then, block 234 directs the master apparatus 64 to compute a correction angle $\Phi_C$, as a function of the angle of the master rotation $\Phi_{DIFF}$ and the component of the master rotation in the misalignment plane L by the relation:

$$\Phi_C = B\Phi_{DIFF} f(L)$$

Where: B is a scaling factor that defines the fraction of $\Phi_{DIFF}$ that should be used in the correction angle $\Phi_C$, for example B=0.5.

f(L) is a function that alters the profile of how the correction angle $\Phi_C$ changes with the plane of orientation change, for example $f(L) = L^3$.

Then, block 236 directs the master apparatus 64 to compute a correction matrix $R_C(\Phi_C, e_{ERR})$ to rotate by the correction angle $\Phi_C$ about the misalignment axis $e_{ERR}$.

The correction matrix $R_C$ is determined by the relation:

$$R_C(\Phi_C, e_{ERR}) = e_{ERR} e_{ERR}^T + \cos(\Phi_C) * (I - e_{ERR} e_{ERR}^T) + \sin(\Phi_C) E_{ERR}$$

Where:

$E_{ERR}$ = the cross product matrix of vector $e_{ERR}$ $$E_{ERR} = \begin{bmatrix} 0 & -e_{ERR3} & e_{ERR2} \\ e_{ERR3} & 0 & -e_{ERR1} \\ -e_{ERR2} & e_{ERR1} & 0 \end{bmatrix}$$

$$I = \text{the } 3 \times 3 \text{ identity matrix} \begin{bmatrix} 1 & 0 & 0 \\ 0 & 1 & 0 \\ 0 & 0 & 1 \end{bmatrix}$$

Then, block 238 directs the master apparatus 64 to modify the end effector base matrix using the correction matrix, $R_C$ by the relation:

$$R_{EEBASE}' = R_{EEBASE} R_C$$

The $R_{EEBASE}'$ value calculated by block 238 is then saved in the sixth store 154, of FIG. 3 as $R_{EEBASE}$.

Then, block 244 directs the master apparatus 64 to re-compute the end effector rotation matrix $R_{EENEW}$ using the new end effector base rotation matrix $R_{EEBASE}$ and store this new end effector orientation as $R_{EENEW}$ in store 164, of FIG. 3.

$$R_{EENEW} = R R_{EEBASE}$$

Where: R is a rotation matrix describing the rotation between the master base rotation matrix and $R_{MBASE}$ the current handle rotation matrix $R_{MCURR}$.

$$R = R_{MCURR} R_{MBASE}^{-1}$$

Then, block 240 directs the master apparatus 64 to location "E" in FIG. 8B to execute blocks 215 and 159 and the end effector positioning and orientation calculation block 116 is ended.

Alternatively referring to FIG. 8E blocks 250 and 252 can replace blocks 238 and 244 in FIG. 8D and the use of base frames $R_{MBASE}$ and $R_{EEBASE}$ to calculate $R_{MCURR}$ and $R_{EENEW}$ can be avoided, requiring consideration of only the reference frames $x_r$, $y_r$, $z_r$ and $x_s$, $y_s$, $z_s$ for the master and slave, respectively, and the task frames $x_1$, $y_1$, $z_1$ and $x_2$, $y_2$, $z_2$ for the master and slave, respectively. In this alternative, the misalignment $R_A$ between $R_m$ and $R_{ee}$ is calculated upon system activation using the relation $R_A = R_m^{-1} R_{ee}$. The master-slave misalignment ($R_A$) is then used to account for the misalignment as the new values of $R_{ee}$ are computed using the relation $R_{EENEW} = R_{MCURR} R R_A$. A correction matrix ($R_C$) is then used in block 250 to adjust $R_A$ each time step using the relation $R_A' = R_A R_C$ until the alignment reaches the alignment criterion.

Referring back to FIG. 3, the kinematics block 118 then directs the master apparatus 64 to use the saved values for $\vec{P}_{EENEW}$ and $\vec{P}_{EENEW}$ to determine the configuration variables. The configuration variables are made available to the motion control block 120 and the motion control block 120 produces the slave control signals representing wire lengths. Referring back to FIG. 8A, block 161 has the effect that the slave control signals based on $\vec{P}_{EENEW}$ and $R_{EENEW}$ are transmitted to the slave computer 74 when the footswitch 170 is not depressed. When the footswitch 170 is depressed the process continues at block 163, and the slave control signals based on $\vec{P}_{EEPREV}$ and $R_{EEPREV}$ are transmitted to the slave computer 74 when the footswitch 170 is depressed.

It will be appreciated that the above routine is executed by the end effector position and orientation calculation block 116 after each sample of the $\vec{P}_{MCURR}$ and $R_{MCURR}$ values is acquired from the control unit 92. Suitable values for the scaling factor B at block 234 and suitable choices for the correction angle function f(L) at block 234 will cause the $R_{EEBASE}$ saved in store 154 to be updated each time the routine is executed, i.e. each time new $\vec{P}_{MCURR}$ and $R_{MCURR}$ values are acquired, until the alignment error $\Phi_{EE\_TO\_MASTER}$ is below the alignment threshold at which time the handle 102 and the end effector 73 are considered to be aligned and no further modification of the $R_{EEBASE}$ value occurs.

Generally, when the enablement signal is in the inactive state, the handle 102 on input device 61 can be moved and rotated and the calculations of $\vec{P}_{EENEW}$ and $R_{EENEW}$ will still be performed, but there will be no movement of the end effector 73. This allows "clutching" or repositioning the handle 102 without corresponding movement of the end effector 73, to enable the end effector 73 to have increased range of movement and to allow the operator to reposition their hands to a more comfortable position within the master translational workspace. For example, referring to FIG. 7, the operator could push the handle 102 in the $z_r$ direction toward the control unit 92 while the enablement signal is active, whereby the end effector 73 is moved in the $z_s$ direction corresponding to the movement of the handle 102. Then, the operator can actuate the footswitch 170 to set the enablement signal inactive and while the footswitch is actuated, withdraw the handle 102 along the $z_r$ axis in the opposite direction, away from the control unit 92, while the end effector 73 remains stationary due to the enablement signal being inactive. Then, the operator can release the footswitch 170 to set the enablement signal active and then continue pushing the handle 102 in the $z_r$ direction toward the control unit 92 while the end effector 73 is moved in the $z_s$ direction corresponding to the movement of the handle 102. Similar effects are experienced with rotational movements of the handle 102 and the end effector 73, when the enablement signal is active and inactive, to achieve a clutching effect in rotation.

The above clutching effect is achieved by causing movements of the handle 102 and movements of the end effector 73 to be made relative to the last-saved master base position $\vec{P}_{MBASE}$ and orientation $R_{MBASE}$ and the last saved slave base position $\vec{P}_{EEBASE}$ and orientation $R_{EEBASE}$ respectively. The master computer 64 stores the current values of the current handle position $\vec{P}_{MCURR}$ and current handle orientation $R_{MCURR}$ signals as new values of the master base position signals $\vec{P}_{MBASE}$ and new values of the master base orientation signals $R_{MBASE}$ respectively, and stores the current values of the end effector position signals $\vec{P}_{EENEW}$ and new end effector orientation $R_{EENEW}$ signals as new values of the slave base position signals $\vec{P}_{EEBASE}$ and new values of the slave base orientation signals $R_{EEBASE}$ respectively, in response to the enablement signal transitioning from the "not active" state to the "active" state. Otherwise, upon release of the footswitch 170, the end effector 73 would "snap" to the absolute position directly mapped to the position and orientation of the handle 102 and this could be dangerous if it were to occur inside a patient because the end effector 73 could tear into tissue or internal organs of the patient with possibly life-threatening effects. In addition, the surgeon would feel somewhat out of control of the end effectors 71 and 73.

While the above described clutching effect is desirable to match the range of translational movement of the end effector 73 with the range of movement of the handle 102 and to reposition the hands of the operator to a comfortable position, it is not desirable for clutching to result in reorientation of the handle within the master rotational workspace because orientation control can become unnatural or unintuitive to the operator when there is a misalignment between the handle 102 and end effector 73. In the absence of a mechanical means to maintain the orientation of the handle 102 it would be difficult for the operator to rotate the handle 102 to cause it to be exactly aligned with the end effector 73 on release of the footswitch 170 so that normal operation can be resumed. In this regard, the codes of the end effector position and orientation calculation block 116 direct the master apparatus 64 to detect a difference, between the current handle orientation signals $R_{MCURR}$ and the new end effector orientation signals $R_{EENEW}$, the difference representing a difference in physical alignment between the end effector 73 and the handle 102 relative to their respective fixed reference frame. In response to detecting the difference, the codes cause the master apparatus 64 to adjust the saved slave base orientation signals $R_{EEBASE}$ to ultimately have values close to the same values as the saved master base orientation signals $R_{MBASE}$ so that subsequent generations of the end effector orientation signals $R_{EENEW}$ cause the slave control signals produced by the motion control block 120 to cause the end effector 73 to be physically aligned with the handle 102 relative to their respective fixed reference frames.

This technique of adjusting the saved slave base orientation signals $R_{EEBASE}$ also has applications in providing a wrist-roll management feature, where wrist roll is measured as variations of orientation of the handle 102 relative to only the z-axis. The wrist roll management feature would have the effect of correcting only for misalignment for the direction in which the end effector 73 and the handle 102 are pointing and not the rotation about the axis 134 of the end effector 73.

Generally, the above described system may cause smooth autonomous motion of the end effector 73 toward alignment with the handle 102, when there is a misalignment between the handle 102 and the end effector 73 without compromising control of the end effector 73 for the operator. In addition, if the alignment error $\Phi_{EE\_TO\_MASTER}$ exceeds the threshold value, the alignment error will always be reduced no matter what direction the handle 102 is moving, unless $e_{DIFF}$ and $e_{ERR}$ are parallel and $f(A)$ is such that $f(A)=0$ when $A=0$.

While specific embodiments of the invention have been described and illustrated, such embodiments should be considered illustrative of the invention only and not as limiting the invention as construed in accordance with the accompanying claims.

What is claimed is:

1. A method of reducing alignment difference between an instrument end effector and an input actuator in a robotic system, the method comprising, by a processor:
    receiving signals representing an orientation of the input actuator;
    receiving an enablement signal that, in an active state, permits a change in the orientation of the instrument end effector in response to a change in the orientation of the input actuator;
    in response to determining that the enablement signal has transitioned to the active state, determining an alignment error between a current orientation of the input actuator and a current orientation of the instrument end effector; and
    while the alignment error is greater than an alignment criterion and the enablement signal is in the active state:
        determining a rotational speed associated with a change in orientation of the input actuator;
        in response to determining that the rotational speed satisfies a threshold rotational speed associated with reducing the alignment error, producing an adjustment control signal; and
        adjusting the orientation of the instrument end effector based on the adjustment control signal to reduce the alignment error.

2. The method of claim 1 wherein determining the alignment error comprises computing an offset angle between a master reference frame in which the input actuator is oriented and a slave reference frame in which the instrument end effector is oriented.

3. The method of claim 2 wherein computing the offset angle is performed while permitting a roll alignment error about the respective z-axes between the slave reference frame and the master reference frame.

4. The method of claim 2 wherein computing the offset angle comprises generating a rotation matrix that carries the instrument end effector orientation at a time of the enablement signal transition into the input actuator orientation at the time of the enablement signal transition and determining the offset angle associated with the rotation matrix.

5. The method of claim 2 wherein the alignment error is determined to be greater than the alignment criterion in response to the offset angle between the slave reference frame and the master reference frame being less than a threshold value.

6. The method of claim 1 wherein producing the adjustment control signal comprises:
    determining a misalignment axis associated with the alignment error;
    determining an axis and an angle of rotation associated with the change in orientation of the input actuator;
    computing a component of rotation associated with the changes in orientation of the input actuator in a direction of the misalignment axis; and
    computing a correction angle for the adjustment based on the angle of rotation of the input actuator and the component of rotation.

7. The method of claim 1 further comprising, in response to determining that the rotational speed does not satisfy the threshold rotational speed, not adjusting the orientation of the instrument end effector.

8. The method of claim 1 wherein determining the rotational speed comprises:
    generating a rotation matrix that carries a previous input actuator orientation into a current input actuator orientation;
    computing an angle of rotation associated with the rotation matrix; and
    computing the rotational speed based on the angle of rotation and a sampling rate for the input actuator.

9. The method of claim 1 wherein producing the adjustment control signal; comprises successively adjusting an orientation of a slave reference frame until the slave reference frame in which the instrument end effector is oriented meets the alignment criterion.

10. The method of claim 1 wherein determining the rotational speed is performed for each change in orientation of the input actuator.

11. A non-transitory computer readable medium storing instructions that, when executed by a processor, cause the processor to execute a method of reducing alignment difference between an instrument end effector and an input actuator in a robotic system, the method comprising:
    receiving signals representing an orientation of the input actuator;
    receiving an enablement signal that, in an active state, permits a change in the orientation of the instrument end effector in response to a change in the orientation of the input actuator;
    in response to determining that the enablement signal has transitioned to the active state, determining an alignment error between a current orientation of the input actuator and a current orientation of the instrument end effector; and while the alignment error is greater than an alignment criterion and the enablement signal is in the active state:
   determining a rotational speed associated with a change in orientation of the input actuator;
   in response to determining that the rotational speed satisfies a threshold rotational speed associated with reducing the alignment error, producing an adjustment control signal; and
   adjusting the orientation of the instrument end effector based on the adjustment control signal to reduce the alignment error.

12. The computer readable medium of claim 11 wherein determining the alignment error comprises computing an offset angle between a master reference frame in which the input actuator is oriented and a slave reference frame in which the instrument end effector is oriented.

13. The computer readable medium of claim 12 wherein computing the offset angle is performed while permitting a roll alignment error about the respective z-axes between the slave reference frame and the master reference frame.

14. The computer readable medium of claim 12 wherein computing the offset angle comprises generating a rotation matrix that carries the instrument end effector orientation at a time of the enablement signal transition into the input actuator orientation at the time of the enablement signal transition and determining the offset angle associated with the rotation matrix.

15. The computer readable medium of claim 12 wherein the alignment error is determined to be greater than the alignment criterion in response to the offset angle between the slave reference frame and the master reference frame being less than a threshold value.

16. The computer readable medium of claim 11 wherein producing the adjustment control signals comprises:
   determining a misalignment axis associated with the alignment error;
   determining an axis and an angle of rotation associated with the change in orientation of the input actuator;
   computing a component of rotation associated with the changes in orientation of the input actuator in a direction of the misalignment axis; and
   computing a correction angle for the adjustment based on the angle of rotation of the input actuator and the component of rotation.

17. The computer readable medium of claim 11 further comprising, in response to determining that the rotational speed does not satisfy the threshold rotational speed, not adjusting the orientation of the instrument end effector.

18. The computer readable medium of claim 11, wherein determining the rotational speed comprises:
   generating a rotation matrix that carries a previous input actuator orientation into a current input actuator orientation;
   computing an angle of rotation associated with the rotation matrix; and
   computing the rotational speed based on the angle of rotation and a sampling rate for the input actuator.

19. The computer readable medium of claim 11 wherein producing the adjustment control signals comprises successively adjusting an orientation of a slave reference frame until the slave reference frame in which the instrument end effector is oriented meets the alignment criterion.

20. The computer readable medium of claim 11 wherein determining the rotational speed is performed for each change in orientation of the input actuator.

* * * * *